US009235977B2

(12) United States Patent  (10) Patent No.: US 9,235,977 B2
 Deutsch (45) Date of Patent: Jan. 12, 2016

(54) SYSTEMS AND METHODS FOR MONITORING CAREGIVER AND PATIENT PROTOCOL COMPLIANCE

(76) Inventor: Richard Deutsch, Annapolis, MD (US)

( * ) Notice: Subject to any disclaimer, the term of this patent is extended or adjusted under 35 U.S.C. 154(b) by 969 days.

(21) Appl. No.: 13/385,483

(22) Filed: Feb. 22, 2012

(65) Prior Publication Data
 US 2012/0212582 A1 Aug. 23, 2012

Related U.S. Application Data

(60) Provisional application No. 61/463,672, filed on Feb. 22, 2011.

(51) Int. Cl.
 *G08B 21/24* (2006.01)
 *G06Q 10/06* (2012.01)
 *G06Q 50/22* (2012.01)
 *G06Q 50/24* (2012.01)

(52) U.S. Cl.
 CPC .............. *G08B 21/245* (2013.01); *G06Q 10/06* (2013.01); *G06Q 10/063114* (2013.01); *G06Q 50/22* (2013.01); *G06Q 50/24* (2013.01)

(58) Field of Classification Search
 CPC .... A61B 5/0013; A61B 5/002; A61B 5/1113; A61B 5/1115; A61B 5/1117; A61B 5/1123; A61B 5/1128; A61B 5/6889; A61B 5/6892; A61B 5/7445; A61B 5/7475; G08B 21/0476; H04N 7/185
 See application file for complete search history.

(56) References Cited

U.S. PATENT DOCUMENTS

| | | | |
|---|---|---|---|
| 2005/0035862 A1* | 2/2005 | Wildman et al. | 340/573.1 |
| 2009/0091458 A1* | 4/2009 | Deutsch | 340/573.1 |
| 2009/0119843 A1* | 5/2009 | Rodgers et al. | 5/611 |

* cited by examiner

*Primary Examiner* — Sath V Perungavoor
*Assistant Examiner* — Peter D Le

(57) ABSTRACT

A system and methods is provided for facilitating, monitoring and recording caregiver and patient compliance with established hospital hand hygiene protocols. The system comprises a 3-D imaging and monitoring assembly and an optional intelligent programmable monitor/sanitizer. Three dimensional imagery tracks a caregiver's movements and location while generating a representative image value. Information acquired by the imaging system determines the proximity of a caregiver to the patient and/or contamination source and determines if the sanitizers provided have been utilized and if so, at an appropriate time and distance from the patient per hospital protocol. While being monitored, a representative Avatar based on physical characteristics derived from three dimensional images of the caregiver and patient may be generated so as to maintain anonymity of both unless a violation of institutional protocol occurs which may be forensically recorded in real-time for analysis.

27 Claims, 14 Drawing Sheets

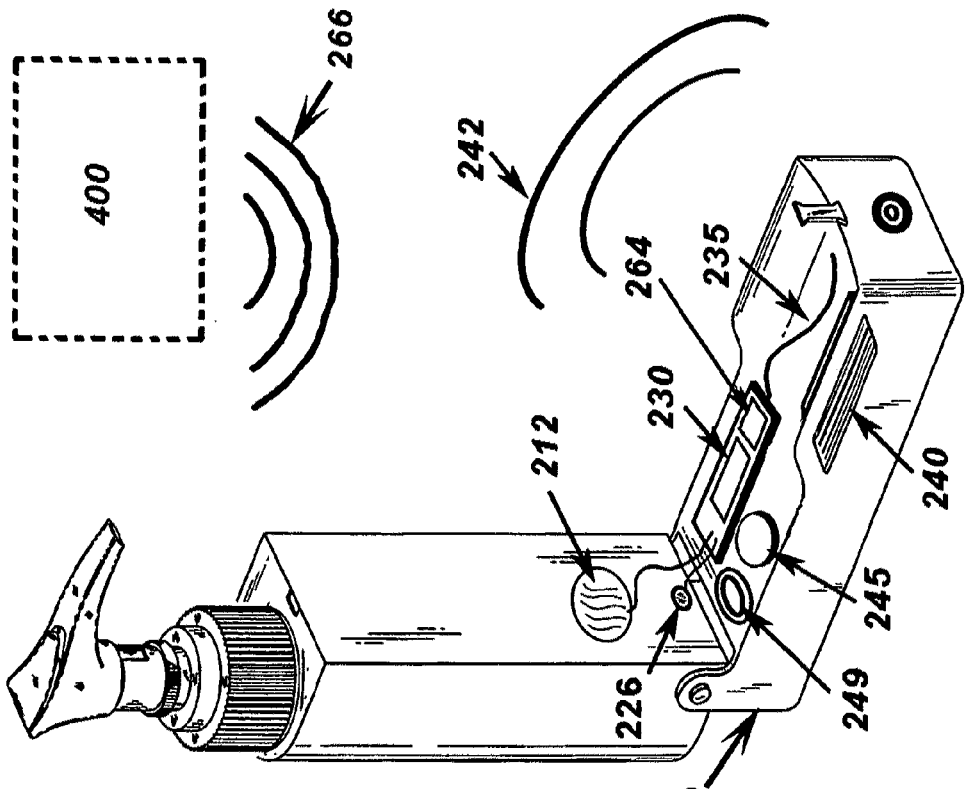
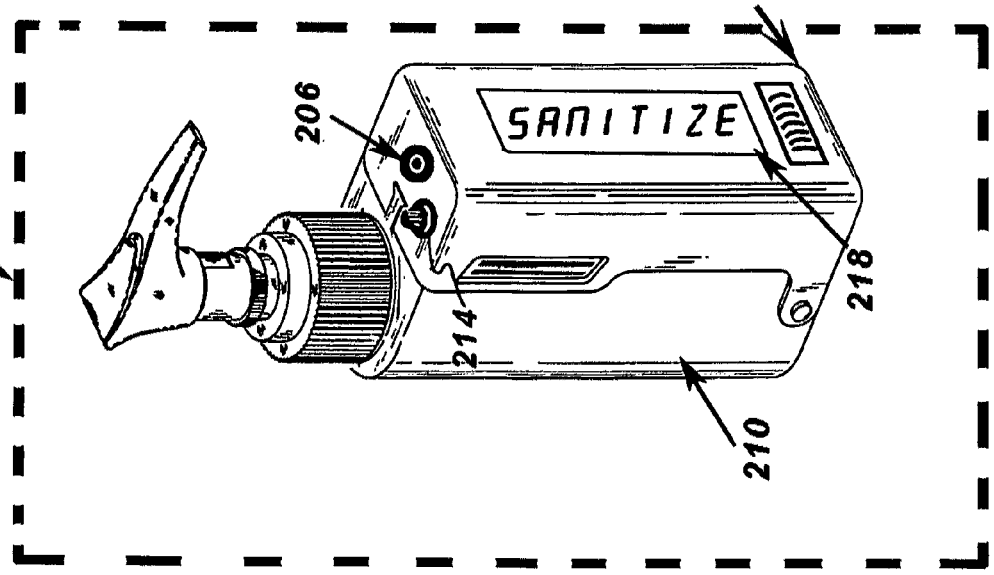

SYSTEMS AND METHODS FOR MONITORING CAREGIVER AND PATIENT PROTOCOL COMPLIANCE

CROSS-REFERENCE TO RELATED APPLICATIONS

This application claims the benefit of U.S. Provisional Application No. 61/463,672 filed on Feb. 22, 2011.

BACKGROUND OF THE INVENTION

1. Field of the Invention

The field of the invention relates to systems and methods for monitoring Health Care Workers, visitors and other person's hygiene practices when attending patients in order to promote compliance with required hygienic protocol while concurrently monitoring actions and conditions of patients thereby protecting patients and staff who may be adversely affected by non compliance with such protocols.

2. Brief Description of the Related Art

The Center for Disease Control, health care facilities and other institutions have recognized the need for promoting personal hygiene among workers. One of the most common practices by such institutions is to post signs in hallways and restrooms reminding workers that their hands must be washed. More sophisticated systems have been developed for monitoring the actions of workers. One such system includes badges worn by workers that are capable of transmitting or receiving information. As discussed in U.S. Pat. No. 6,236,317, workers are provided with badges that detect entry into an area that may be unsanitary and alert the workers to this fact. If a worker subsequently washes his hands or activates a disposable glove dispenser following such exposure, the alerting function of the badge is deactivated. If appropriate action is not taken by a worker, a violation is recorded by the badge or a system controller.

U.S. Pat. No. 6,882,278 describes another system that monitors compliance with recommended hand-washing practices. The system includes a hand-washing detector and an event detector such as a motion detector that detects an event such a person entering or leaving a room. A control unit determines whether a person has washed his hands within a predetermined time period before entering the room.

U.S. Pat. Nos. 6,727,818 and 6,975,231 disclose other systems for promoting hygienic practices. The first mentioned patent discloses a system that tracks the movements of health care workers throughout the facility and within a patient's room. The health care workers are provided with badges that transmit ID information to sensors located in the hallways and rooms of the facility, which in turn transmit location information to a master station. ID information is also transmitted to wash sink sensors to indicate whether the health care worker has washed his hands. If the health care worker enters a patient contact zone in the patient's room without having complied with the required hand washing procedure, an alert is provided by the health care worker's badge and/or other alerting devices located on the patient's bed or in the patient's room.

A time delay may be employed before a warning alert is provided so that an alert is not triggered by a health care worker who is only briefly in the patient contact zone. U.S. Pat. No. 6,975,231 discloses a system employing sets of detectors located just outside and within a patient's room. These detectors are actuated sequentially as a person enters the room and the time between their actuation is monitored in determining whether a person has entered the room. A determination is made as to whether the person has washed his hands within a predetermined period of time, and a warning signal is generated if the hands have not been washed within the set period.

U.S. Pat. No. 8,090,155 Lacey discloses the use of a camera to monitor the hands so as to determine hand washing activity but does not provide a means to address the issue of identifying whose hands are being monitored and their relationship to the patient.

U.S. Patent No. 2011/027740, U.S. Pat. No. 8,110,047 U.S. Pat. No. 8,094,029, 20050248461, U.S. Pat. No. 8,085,155, U.S. Pat. No. 7,898,407, U.S. Pat. No. 7,855,651, U.S. Pat. No. 7,818,083 U.S. Pat. No. 7,682,464, U.S. Pat. No. 7,605,704, U.S. Pat. No. 7,375,640 and U.S. Pat. No. 7,372,367 hygiene monitoring schemes all require the use of RFID badges. The application of RFID as the backbone of almost all currently available hygiene monitoring systems ignores the restrictive nature presented by this technology. RFID limitations become apparent when considering the absence of an RFID badge being carried by a caregiver, Health Care Worker or visitor allows the potential hygiene violator to then become invisible to the associated monitoring system. The use of radio waves opposed to three dimensional visual imaging as a means of determining location and proximity, are subject to inconsistencies in ranging dependent on many outside variables, particularly in a RF "noisy" hostile hospital environment. Radiating in a fixed circular or elliptical pattern, the application of such radio waves or IR beams opposed to three dimensional imaging for near proximity monitoring is extremely limited in resolving "the finite point of care", the actual probable contamination point between the rectangular shaped patient and/or bed patient and the HCW or visitor.

The benefits of signs reminding people to sanitize their hands are believed to be limited in effectiveness. Interactive systems that notify a person that he has not performed a required procedure are likely to result in better compliance, particularly if coupled with a system that makes a record of violations. It is important, however, to avoid "false alarms" that would cause a person to be notified of a compliance issue unnecessarily or record a violation where no issue of potential contamination is present. For example, a number of persons entering a hospital room do so for purposes other than treating a patient, and accordingly will not contact or even closely approach a patient. A system that signals hygienic warnings for such persons may tend to be ignored over time as too many warnings are issued during the course of a day. To the greatest possible extent, a system should display warnings only with respect to persons who actually come in close proximity or contact with a patient and have not complied with required hygienic practices before doing so. It is also important to detect unauthorized persons who may approach or come into contact with a patient regardless of whether they are wearing a badge or other type of transmitting/receiving apparatus. Additionally, as patients are often capable of moving from their beds and in and out of their rooms, warnings due to such movements should either not be displayed or reflect the fact that they are patient-initiated when not within prescribed hospital protocol and patient injury has or may result from such action. Health Care Workers, visitors and HCWs attending aforementioned patients shall all be considered as the same within this description and such terms to be used interchangeably.

The observation of Health Care Workers (HCW) and patients is not limited to only monitoring hygiene practices. Tens of thousands of serious injuries to patients occur every year when those patients, not capable of ambulating without assistance attempt to leave their bed unassisted. As patients are often capable of moving in and out of their beds and rooms as well, warnings due to such movements should either be displayed or reflect the fact that they are patient-initiated when not within prescribed hospital protocol and the probability of patient injury has or may result from such action. Additionally, certain specific anatomical movements involving the patients limbs and/or body may be indicative of a medical emergency, requiring immediate medical assistance Monitoring and interpretation of these actions and the results of the patient violating hospital protocol while attempting to leave their bed or room, can be accomplished by the methods described herein.

SUMMARY OF THE INVENTION

Methods, systems and system component are provided to facilitate compliance with healthcare protocol in a hospital or other health care facility. In accordance with one aspect, a method is provided that includes capturing three dimensional images of a person and a patient within a room. The person could be, for example, HCW, a caregiver or a visitor. The method further includes tracking the location of the person within the room, determining whether the person is in close proximity to or in contact with the patient by determining the relative positions of the three dimensional images, determining whether the person has actuated a sanitizing device, and determining whether a caution or warning signal should be generated based on whether the person in close proximity or in contact with the patient has actuated the sanitizing device. The term "close proximity" refers to a position wherein the person is within arm's length of a patient support apparatus such as a hospital bed, a crib or the like upon which a patient is positioned. This can be somewhat greater than arm's length from the patient himself. The method may further require actuation of the sanitizing device in a specific location within the room depending on the type of sanitizing device that is employed.

In another aspect, a method is provided that includes capturing a three dimensional image of a person within a room, tracking the location of the person within the room, determining whether the person has come within a first distance of a patient by determining the position of the three dimensional image, and determining whether the person has come within a second distance of a patient that is closer to the patient than the first distance and in close proximity to the patient by determining the position of the three dimensional image. The method further includes determining whether the person has caused the actuation of a sanitizing device. A first selected message is generated following detection of the person sequentially coming within the first and second distances of the patient without having caused the actuation of the sanitizing device.

In a further aspect, a method includes providing a sanitizing device including a memory, a transmitter and a receiver to a person. A three dimensional image of the person within a room is captured and an image value associated with the three dimensional image is created. The method further includes associating the person with the sanitizing device by transferring the image value to the memory of the sanitizing device. A portable sanitizer/monitor that can be associated with a captured three dimensional image of a person is also provided, obviating the need for assigning personal ID's to a sanitizer/monitor.

In a further aspect, a method includes capturing a three dimensional image of a person who has entered a room in a medical care facility, creating an avatar associated with the three dimensional image, tracking movement of the avatar within the room, determining whether a sanitizer has been activated, and generating a signal reflecting the sanitation status of the avatar based on whether the sanitizer has been activated. A caution or warning signal is generated based on detection of the avatar in a selected position within the room and the sanitation status of the avatar.

A system provided in accordance with a further aspect includes a three dimensional imaging system operable to generate an image value derived from a three dimensional image of the physical characteristics of a person and track the person within a room. A portable sanitizer/monitor is operable to receive the image value from the three dimensional imaging system, create an identification value reflective of the image value, and wirelessly transmit the identification value upon actuation of the portable sanitizer/monitor for sanitizing purposes. A processing assembly is communicable with the three dimensional imaging system and operable to receive the identification value from the portable sanitizer/monitor, associate the image value with the identification value, determine whether the portable sanitizer/monitor was actuated in a specified location within the room, and transmit a hygienic status signal based on receipt of a transmission from the portable sanitizer/monitor including the identification value and the location of the person associated with the image value within the room at the time of the transmission from the portable sanitizer/monitor.

A system provided in accordance with a further aspect includes a sanitizing device, a three dimensional imaging system operable to detect specific kinematic hand motions at the sanitizing device and transmitting a signal responsive to detected specific kinematic hand motions, a processing assembly operatively associated with the three dimensional imaging system for receiving the signal and generating an output signal in response thereto, and a indicator device operatively associated with the processing assembly for displaying a message upon receipt of the output signal. The sanitizing device may be, for example, a sink or a fixed hand sanitizing device.

A monitoring system in accordance with a further aspect includes a projected pattern three dimensional IR imaging camera assembly capable of capturing a three dimensional image of a person such as a HCW. A processor assembly is operative to extract information and generate feature vectors from the three dimensional image so as to analyze motion and position of the detected person in order to determine if such person moves into or contacts a desired or un-desired entity, location or position.

A processor and operative firmware determine the person's sanitized status by monitoring and associating his/her activation of an associated sanitizing device and generate a hand washing protocol compliance indication based on analysis of the images of the person's location and sanitizer activation.

Other features and advantages of the subject matter disclosed herein will become apparent from the following detailed description of illustrative embodiments, which is to be read in connection with the accompanying drawings.

DETAILED DESCRIPTION OF THE PREFERRED EMBODIMENTS

A system for monitoring physical contact with or close proximity to a patient or medical equipment is provided. The system is capable of determining whether the person making such contact or near contact is in compliance with institutional hygienic protocol, and particularly hand-washing rules. It is further capable of determining whether a person who enters a patient's room presents a possible contamination threat irrespective of whether that person is wearing a monitoring device. A three dimensional identity, gesture and position imaging and monitoring system (heretofore referred to as the three dimensional protocol monitoring system 100) capable of electronic depth perception is provided to monitor the presence and actions of persons who may be a patient or approach a patient. The imaging system is preferably comprised of one or more video cameras with image sensors cooperatively associated with an operating system and capable of communication with a controller. To promote compliance with institutional hand washing rules, violators of such rules may receive audible, visual warnings while records are made of their rule violations. While the invention is capable of modification, the specification which follows provides exemplary and preferred embodiments. It should be understood that the invention is not intended to be limited to the particular embodiments disclosed herein, particularly that three dimensional imaging may be accomplished by alternate configurations of a plurality of cameras and operatively associated software and hardware different from the configurations referenced and described herein, but on the contrary is intended to cover all modifications, equivalents and alternatives falling within the spirit and scope of the invention.

Various systems have been developed for generating and analyzing three dimensional images and would be useful for the purposes of the present invention. three dimensional imaging via projecting composite images of modulated light are described by Hassebrook et all in U.S. Pat. No. 7,844,079. Depth mapping using projected patterns by Freedman et all U.S. Pat App. 20100118123, three dimensional multiple person tracking by such method described by Polzin et all U.s. Pat App. 20100303289 and three dimensional gesture recognition by Perez et all U.S. Pat App. 20110007142 which are all incorporated by reference herein. Recognition of an individual from a group via facial recognition is described by Turk et all in U.S. Pat. No. 5,164,992 illustrates the use of 2D facial imaging for selecting an individual from a group. Additionally, various systems have been developed for capturing simple 2D image of an individual and comparing such image to some form of a data base reference either as means of identification or as the operator of a sanitizing device in a hospital environment as illustrated by Kobiasz U.S. Pat App. 20090051545 which is incorporated by reference herein.

In the following detailed description, references are made to the accompanying drawings that form a part hereof, and which are shown by way of illustration, specific embodiments, or examples. Referring now to the drawings, in which like numerals represent like elements through several figures, different embodiments of a HCW and patient compliance system will be described. The preferred embodiment of the system shown in FIG. 1 includes a digital image recognition system that incorporates a three dimensional imaging system capable of determining depth as well as surface deformations which incorporates one or more digital cameras and an image projector arranged to view a scene. The viewed scene would include a patient's room, a patient, a patients bed, an attending care giver, a fixed or mounted sanitizer, an image processor associated with a three dimensional protocol monitoring system 100, a primary controller, an illumination source, a human form detection and processing routine and a command annunciator providing audible or visual cues relating to whether compliance with hospital hygiene protocol or safety has been met. While the annunciator preferably provides audible and/or visual feedback to the HCW/visitor or patient under observation it may also function as a means of wirelessly communicating directly or indirectly to a central data system at a remote location (not shown) for the generation of a compliance report reflecting information relating to the presence of a HCW and/or patient and their compliance with hospital guided patient care and hygiene protocol.

The system 100 employed within the patient's room so as to provide a passive means of monitoring an individual's physical location and movements so as to determine caregiver's compliance with hospital hygiene protocol and a determine the significance of a patient's placement and motions. Configuration of three dimensional imaging cameras 420 configured with an infrared pattern generator and projector 410 capable of projecting composite images of light modulated patterns mounted in a manner that detect whether a HCW 600 is moving towards or standing near the patient. If the change in position is insignificant the device will not trigger. The three dimensional IR imaging system 440 comprised of hardware along with operating and computational logic form a means of inputting location and movement information into the three dimensional monitoring system 100. Imaging system 440 provides vision to the three dimensional protocol monitoring system 100. The intelligence to decide when to detect and what to detect rests with the operating system software and firmware 492 associated with a system-on-a-chip three dimension image processor 490. The three dimension image processor 490 extracts information features from the images and generates feature vectors based on the features, including body, arm and hand shape vectors, and executes a classifier with the vectors to determine the poses. The processor uses edge segmentation and pixel spatio-temporal measurements to form at least some of the feature vectors FIG. 2.

The camera is configured so it will preferably detect a caregiver who moves into or extends an arm into the patient care area 840 or contacts the patient's support device or associated medical support equipment to include their intravenous apparatus. In the preferred embodiment, the mechanism for determining HCW presence within the first distance patient control area 860 and the second distance, patient care area 840 defined as an arm's length from the patient or their support device, is accomplished by the three dimensional imaging assembly 400 which incorporates a three dimensional IR imaging device 440, comprised of digital motion detection and image tracking hardware and system's firmware 492 associated with the three dimension image processor 490 that is capable of processing the image of any HCW 600 detected by three dimensional imaging three dimensional imaging assembly 400. The location of the three dimensional IR imaging device 440 is such as to provide a viewing area for detection by the digital camera(s) of all relevant persons in relation to the patient, configured in such a geometric shape as to provide motion and image detection in system detection area 888 surrounding the patient 920 or patient's support apparatus 922.

The three dimensional protocol monitoring system 100 may distinguish very small distances of proximity between a HCW the sanitizer and the patient if programmed to do so. The use of multiple three dimensional IR imaging devices 440 incorporated within three dimensional imaging assembly 400 may alternatively provide redundancy, ensuring that a Health Care Worker caregiver or visitor (these terms to be used interchangeably) will indeed be detected by at least one of the associated imaging camera assemblies. Charge transfer sensors may be integrated into the afore mentioned monitoring system for detecting patient or bed contact or near contact, as demonstrated in Deutsch U.S. Pat. No. 7,893,842 which is incorporated by reference herein. It will be appreciated that different three dimensional imaging camera systems may have different fields of view and viewing ranges as deemed appropriate.

In the preferred embodiment, the system 100 is configured to track the hygiene status, presence, proximity and extremity movements of a HCW 600 in relation to the patient 920, the patient's support apparatus 922 or other patient related equipment (not shown) e.g. ventilator, central IV etc. in one or more increments of increasing or decreasing proximity with or without the use of a monitoring badge. The system employs a three dimensional imaging system that tracks not only the HCW's torso but also tracks the position and motion of the HCW's extremities. When the imaging assembly system's firmware 492 determines the co-incidence of the HCW's hand and the patient 920, the patient's support apparatus 922, associated life support apparatus e.g. ventilator or central line (not shown) this image registers as cross contamination contact 930 or an opportunity of cross contamination within the deterministic kinematic logic of image processing system's firmware 492. Additionally, the visual determination by system 100 of near contact of a HCW hand with an associated fixed base sanitizer 500 for a finite period of time may be interpreted as sanitizer activation. The configuration of the three dimensional protocol monitoring system 100 facilitates the ability to determine and record hand washing rule compliance such that audible and/or visual responses related to the specific distance, direction of travel and hygiene compliance of the health care worker to and/or from the patient can be made with or with the use of a monitoring badge.

Upon detection of the caregiver in system detection area 888 by three dimension image processor 490 associated with middleware logic in processor 492 causes the commencement of tracking and motion analysis of the monitored caregiver 600 by imaging system 440. The detection of specific deterministic actions by the monitored caregiver as referenced against a library of deterministic actions contained within middleware 492 will cause imaging system 440 communicate with primary controller reflecting the coincidence of same. Specific hygiene rules may apply to detection of the caregiver in select area to include system detection area 888, patient control area 860 and patient care area 840. Similarly, detection of caregiver motions to include placement of hands within a specific zone for a finite period of time i.e. near a sanitizer to indicate hand sanitizing or placement of a monitored caregivers hands near, but not limited to, a patient, a patient's support apparatus a patient's medical device, or a patients central line IV, may cause the generation of an alert signal to the primary controller. Additional visual detection of contact or near contact by the monitored caregiver with areas of know contaminated surfaces such as walls, doors and medical equipment may cause the generation of an alert signal to the primary controller indicating same feature vectors are representative of the dimensional physical structure and juxtaposition of individual segments representing a full or partial entity. Algorithms in middleware 492 consolidate these visually acquired feature vectors into an image value 444 representing a composite entity. The composite image value can then be associated with a specific entity to include a monitored caregiver. Once the caregiver is assigned a representative image value identifying them and tracking their location and motions become a relatively simple process.

Tracking the caregiver's location and motions may be assisted by the generation of a proposed but not required representative Avatar. Processing information from the caregiver's representative Avatar reduces computational overhead as well as providing anonymity to the caregiver. It is important to note if Avatars are incorporated as representing images of the patient that the utilization of the three dimensional protocol monitoring system 100 for monitoring the patient as provide assures a means whereby any recordation of the patient may be represented by an image associated Avatar, and as such the patient will be able retain dignity, modesty and anonymity at all times.

The creation and tracking of a representative Avatar may minimize computational overhead and establish a sense of privacy to both patient and HCW in lieu of their actual image. The representative three dimensional Avatar may be assigned the HCWs image value 444. This image value 444 is derived from the computations shown in figure description 6/7. The actual image of either person or HCW need not be recorded or stored in any form of digital memory or may be recorded just prior to, or subsequent to a hygiene protocol violation in real-time for forensic analysis. Subsequent to the Avatar's creation and association with an internal identification number (image value 444) the 3-D imaging system can readily identify the Avatars location 312 or the person 600 within the area of viewing. Since hand hygiene is one of the most important features of hospital protocol, the use of a hand sanitizer within the patient's room at the appropriate time and place is of utmost importance.

As the caregivers' (Avatar's) position and motion is being constantly tracked, the activation of a sanitizer by a specific person or representative caregiver (Avatar) is observed and noted. Hand sanitizing may consist of actuation of a fixed base sanitizer 500, portable monitor/sanitizer 250 or the detection of hand washing gestures 314 at a sink 510 thereby generating a "Hands Sanitized" signal. In its simplest form, the visual detection by imaging system 440 of the placement of the caregivers hand(s) in close proximity to the sanitizers fluid exit port for a pre-determined period of time may be considered activation of a "touchless" sanitizer and a successful sanitizing event. The known deterministic three dimensional visual features and gestures of such actions will be recognized by the system's firmware 492 as reflective of successful hand washing. Alternately, successful handwashing may be determined by actuation of electrical switches associated with the sink or sanitizers. Upon detection of a person entering the patient's system detection area 888, a representative image value 444 or Avatar is created by three dimension image processor 490 as part of three dimensional imaging assembly 400 or alternately an image value is created in step 318 by three dimension image processor 490 as part of fixed base sanitizer 500 imaging system. Subsequent to the generation of an image value 444 image by three dimension imaging assembly 490 such image value information is forwarded to primary controller 360 and stored in controller memory 466.

A wireless monitor may be incorporated into the three dimensional protocol monitoring system 100. The monitor may operatively associate with a portable sanitizer as an assembly 250. The monitor provides a means of ascertaining exactly which individual within a plurality of caregivers has activated their sanitizer at an appropriate time and location per hospital hygiene protocol. The monitor/sanitizer is operatively associated with the primary controller 360. The primary controller operates co-operatively with the imaging system 440 in such a manner as to receive image value information 444 and operating information relating to coincidence of the caregiver and/or Avatar with specific objects and spaces via a serial buss 488. In the proposed system, configuration of the three dimensional protocol monitoring system 100 incorporates a monitor/sanitizer, (though not required). Initial detection of the caregiver's (Avatars) entry into a patient's room causes a contaminated area reset transmitter 724 to autonomously transmit signal 777 causing identification information, to include previously programmed image value 444 and hygiene status coding, to be erased from the caregiver's monitor's memory. Caregivers subsequent entry into system detection area 888 causes imaging system 440 to begin a detection and image analysis process which includes an evaluation of the of the caregivers physical form and function so as to generate an image value derived from feature vectors of the caregiver's image.

Subsequent to the caregivers entry into system detection area 888, imaging system 440 causes the generation of image value 444 which in co-operation with operating memory 140 and firmware 139 of primary controller 360 is stored in for future reference. Primary controller 360 transceiver 264BRX/TX proceeds to forward this image value information from controller memory to aforementioned portable monitor/sanitizer 250's memory 234 via its transceiver 264A-RX/TX and CPU 230 carried by monitored caregiver 600. This process effectively programs the monitor monitor/sanitizer with a unique identification code reflecting the feature vector characteristics of the monitor bearer in the form of a readable image value 444.

When monitor/sanitizer 250 is activated in the course of hand sanitizing a "hands sanitized" an activation signal inclusive of the image value 444 plus a hand sanitized code is sent back to and received by the primary controller 360 via transceiver 264B-RX/TX. Upon receipt of the aforementioned image value code indicating a successful hand sanitizing by transceiver 264 RX/TX of primary controller 360 a comparison is made with data stored in primary controller memory 466 indicating which monitored caregiver has activated their sanitizer via their now assigned identifying image value. This information may be processed by firmware logic 140 contained within data memory 139 of primary controller 360 to determine if such "hand sanitizing" was accomplished at an appropriate location as determined by referencing the observed activation location with acceptable sanitizing locations stored in memory 140 visually acquired via three dimensional imaging. Annunciators 418/518 associated with primary controller 360 or three dimensional assembly 400 may indicate successful sanitizing or lack thereof. The tracking of multiple caregivers' locations and interactions is simplified as well as maintaining HCW anonymity by the low informational overhead carried in providing Avatars with identifying "image value" identifiers 444 for each individual as compared to the alternate of analyzing "real-time" three dimensional images of a HCW's hygiene protocol compliance. Cross contamination contact 930 or near contact between HCW/Avatar 612 and patient Avatar 920 is determined by the ability of three dimensional IR imaging device 440 to precisely monitor extremity motion and locate juxtaposition of entities within its field of view. Additionally, referencing a library of known acceptable and non-acceptable deterministic movements and positions of the Avatars via information stored in rewritable memory in the form of fixed or removable memory 466 associated with three dimensional imaging assembly 400 allows for the determination of acceptability of fine hand movements such as physical or near contact with patient, patient support apparatus or sanitizer 500. 316. Analysis of images collected by 3 dimensional infrared camera 410 associated with three dimension image processor 490 and 492 indicating coincidence or convergence of HCW's hand, body or Avatar with the patient or patient associated medical devices causes three dimension image processor 490 to output control signals to primary controller 460 via bi-directional buss 488. Visual determination of contact between caregiver 600 and select entities will then cause logic functions of the three dimension image processors 490 and 492 with associated processing logic to determine if contact between HCW and patient was initiated without or prior to a hand sanitizing action taking place step 330. Records and images of hygiene protocol violations and compliances may be stored on fixed or removable memory 466 of three dimensional imaging system 400 or primary controller 360 for later review.

Optionally, concurrent image value data 346 from the image processor is available for referencing to an external data base 349 via bi-directional buss 488 for determining absolute identity of HCW by comparison with a data base of known image values and identities 350 or communicating with an associated identification method if present. If sanitizing has not been accomplished prior to this contact, the primary controller will cause the remote annunciators 418 & 438 to display a warning message 332 and cause the patients room to be illuminated with visible light 324 to allow a recording 326 by VGA color camera 430 of the identifying image 328 of the violator in real-time imagery on data memory 340 as well as imprint the image with a RTCC (real time clock calendar) stamp 336. An additional audio warning may be generated 338 concurrently while imagery of the actual violation is recorded on a data memory 340. If HCW complies with required hospital hand sanitizing protocol a complimentary protocol compliance message is generated on associated annunciators 334.

BRIEF DESCRIPTION OF THE DRAWINGS

FIG. 9A is a perspective view illustrating a portable sanitizer dispenser;

FIG. 9B is a perspective view thereof showing the portable sanitizer dispenser in an open position adapted with a monitor to be worn by a health care worker;

FIG. 1, diagrammatically represents a hospital room is equipped with a three dimensional protocol monitoring system 100 including a light source 416 for monitoring compliance with institutional hand washing rules and patient safety. A patient 920 is shown within a hospital bed 922. both of which are located within a patient care area 840 while being attended to by HCW 600. The room includes an entrance, and the room area within the entrance may be considered a contaminated area 865. As shown, contaminated area reset transmitter 724 is positioned just above the room entrance capable of generating a signal 777 for clearing and encoding a portable monitor sanitizer carried by a caregiver. A remote annunciator 438 is located just outside the room. A fixed base sanitizer 500 and a sink 510 in view of said sanitizer is shown within the patient's room, but additional or alternative sanitizers may be located within the patient's bathroom or in other suitable locations. The hand sanitizer includes a sanitizer activation sensor 508 and a transceiver capable of generating an encoded compliance signal 509 reflective of such activation. It further includes an annunciator 518, which may be in the form of an LCD display. The hand sanitizer shown 500 is a "bag-in-box" type dispenser that receives a bladder filled with soap or other sanitizing agent. A three dimensional IR imaging devices 440 is positioned above the patients patient support apparatus. Location of imaging device 440 is configured in a manner so as to determine the hygiene protocol compliance of those persons entering and leaving the patient as well as to provide a means of viewing, in three dimensions, a caregivers visible actions within system detection area 888 which encompasses the first distance, patient control area 860 and second distance, patient care area 840 closer to the patient which is in proximity to the patient and patient's support apparatus 922. It will be appreciated that the room may contain more than one patient and more than one patient care area. A processor and operating system within sanitizer 500 is provided capable of communicating with one or more of the annunciators 418. a system data interface 462, a speaker 456, and transceiver to transmit and receive an encoded compliance signal 509 from the fixed base sanitizer 500. A removable memory 466 is provided to store additional personal and medical information 429 relating to the patient's condition and care and cause the display of such information to include the caregiver's hygiene status 428 on one or more of the annunciators 418.

FIG. 2 diagrammatically illustrates the juxtaposition of the three dimensional imaging camera system to include the IR image projector of the imaging system so as to visually distinguish a HCW's identifiable dimensional characteristics. The determination of these characteristics results in the creation of a virtual Avatar associated with the HCW under observation, thereby representing the movements, gestures and positions of the Health Care Worker within the system detection area 888 as the HCW actually contacts the patients room surroundings, the patient, the patient's support apparatus 922 or associated life support apparatus e.g. central line (not shown). Such cross contamination contact 930 will result in the generation of an alert signal by three dimension image processor 490 reflecting such contact. Three dimensional imaging provides distinct advantages to planar 2-D images in that considerable more information is available for comparison and analysis as well as robustness of identifying the image when only partial image segments are available for comparison to a reference image. Additionally, positional and depth information, both relative and absolute, can be readily derived from the generated three dimensional image. The three dimensional protocol monitoring system 100 preferably allows for simultaneous monitoring of multiple contiguous areas. A patient control area 860 may surround a patient's bed and define one patient care area 840 from other patient care area that may lie within a single room. In a typical hospital situation where more than one bed is located in a room, conventional PIR motion detectors, RF signal strength triangulation or time of flight will not provide the geometry and distance resolution to differentiate one patient care area 840 from another. Visual monitoring with almost infinite special resolution is accordingly preferred for this purpose. The camera system components required for generating and processing the three dimensional protocol monitoring system 100 as described, is currently commercially available as an assembly. Reference is made and included herein to Microsoft/Prime Sense "KINECT" game control system Latta et all U.S. Pat. App. 2010/0199228. which is incorporated by reference herein FIG. 3 provides further details of the three dimensional infrared imaging device 440 intended to monitor a patient 920 and/or health care workers attending a patient. The preferred three dimensional imaging system includes a first infrared pattern generator/projector 410 capable of projecting a composite image of modulated light patterns that are then reflected and distorted by the presence of a HCW, patient and objects within the scene in which they appear. A co-operating monochrome depth image camera 420 is configured to view the reflected pattern distortions created by the objects within the scene. The imaging information received by the monochrome camera is interfaced with a three dimension image processor 490 utilizing edge segmentation and pixel spatio-temporal measurements to form feature vectors while executing sophisticated parallel computational algorithm to decipher the received light coding and produce a depth image of the scene and its inhabitants.

The image processor in co-operation with firmware 492 analyses motion of the body and movement of the body and extremities as they move in desired poses, and durations of pattern movement and then comparing this acquired data with a library of know deterministic kinematic images and motions deriving definitions for certain gestures and positions. Additionally, though not required, a conventional VGA color image camera is incorporated so as to view the identical scene in order to provide robustness to the image quality. The three dimension image processor 490 performs a process called "registration". The registration process's resulting images are pixel aligned meaning that every pixel in the color image is aligned to a pixel in the depth image. The resulting data and logic generated by the system's firmware 492 is then communicated to the primary controller 460 on bi-directional buss 488.

Figure 4:
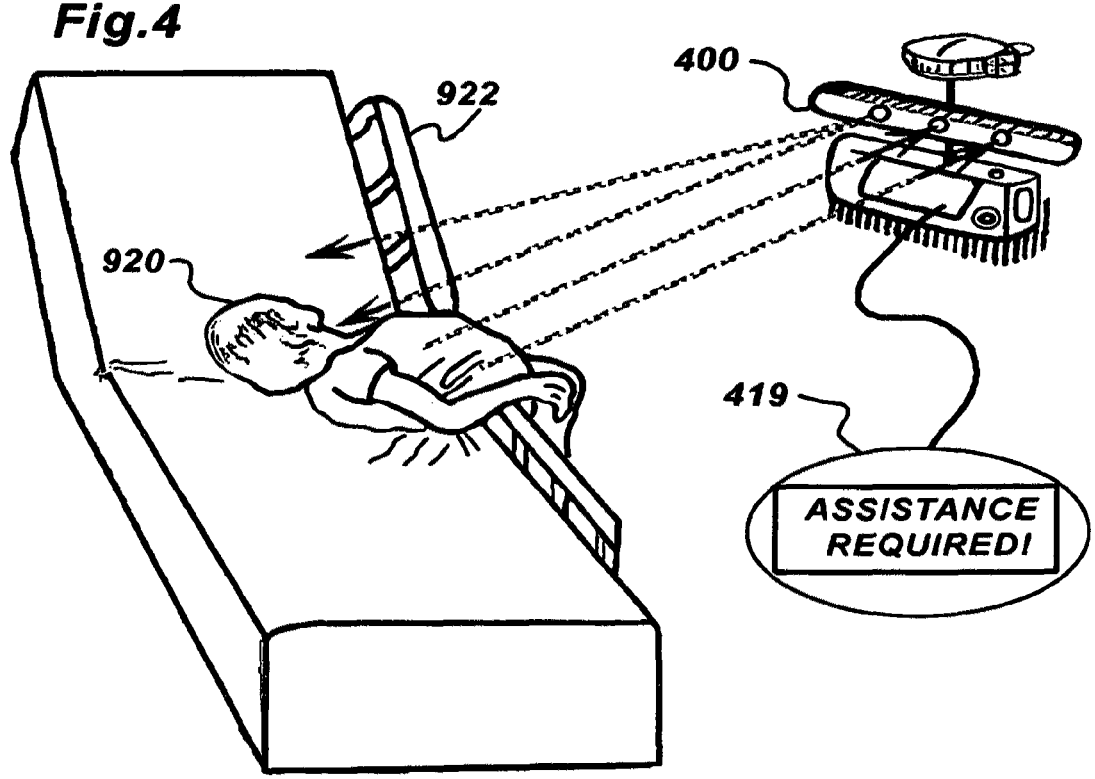
FIG. 4 is a perspective view of a patient requiring immediate assistance being imaged by a three dimensional imaging monitoring system.

FIG. 4 is a perspective view of a three dimensional image monitoring system detecting the position, location and movement of a patient 920 who has partially fallen out of patient's support apparatus 922. This juxtaposition of patient and bed is recognized by the image deterministic middleware incorporated into the three dimensional IR imaging device 440 of the imaging three dimensional imaging assembly 400 as being indicative of an emergency condition. The primary controller 460 associated with imaging assembly then generates an "assistance required" message 419 that appears on one or more remote annunciators 438.

Figure 5:
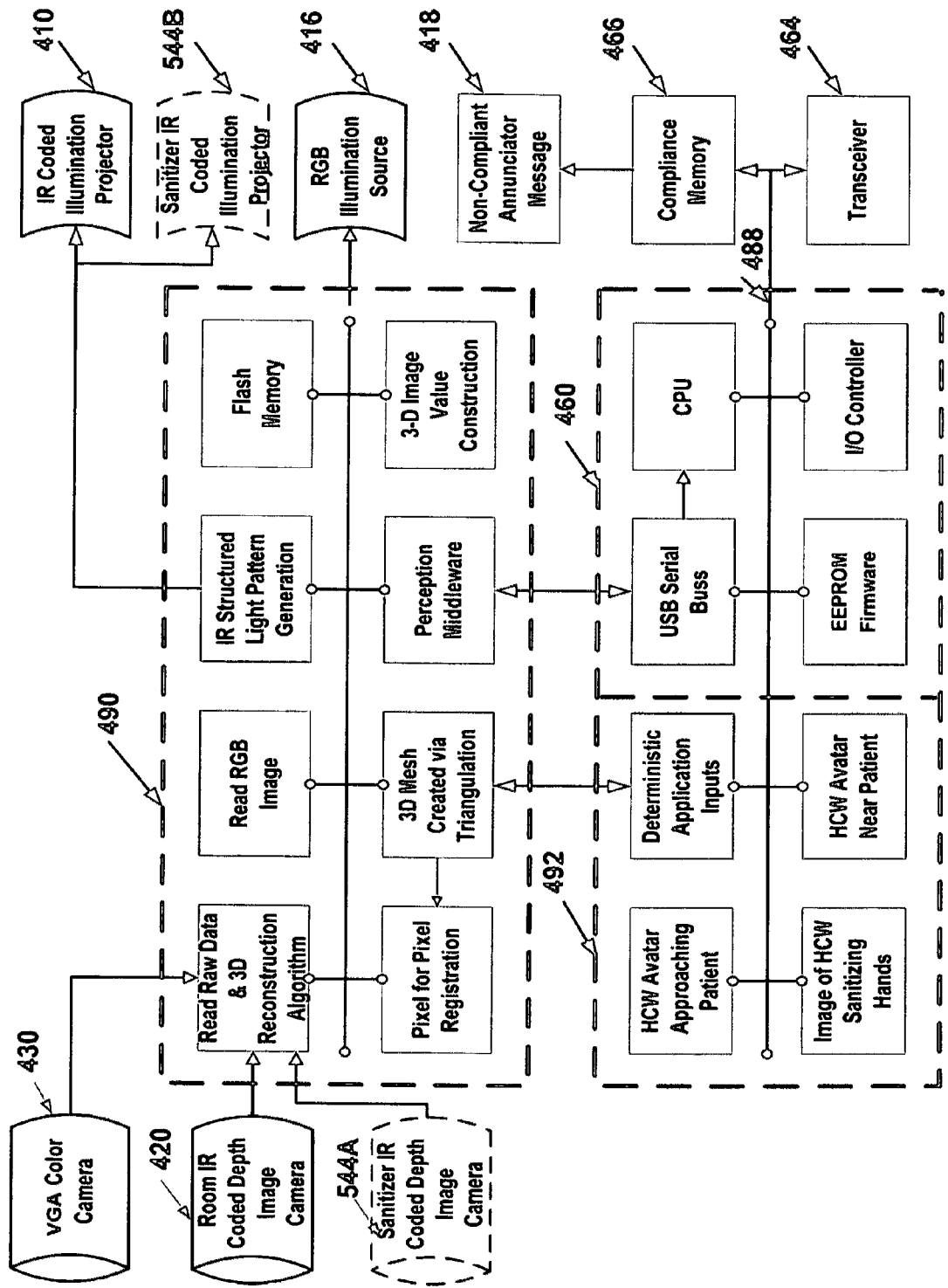
FIG. 5 is a schematic illustration of a three dimensional imaging system used by the monitoring system.

FIG. 5 schematically illustrates the details associated with retrieving depth and identifying gesture and motion information and the creation of an Avatar from a three dimensional image of at least one HCW or patient. Hassebrook et al U.S. Pat. No. 7,844,079, Prime Sense and Freedman et al U.S. App. No 2010/0118123, which is incorporated by reference herein providing a PS1080-A1 commercially available three dimension image processor 490 that is integrated into Microsoft's currently available Microsoft/Prime Sense "KINECT" game control system Latta et all U.S. Pat. App. 2010/0199228 which is incorporated by reference herein. The imaging system's processing logic in firmware 492 along with the three dimension image processor 490 and VGA camera 420 and projector 410 form the three dimensional infrared imaging device 440 that tracks 48 points on an individual's body, mapping these points to a digital reproduction of that person's body shape and skeletal structure including facial details thereby creating a virtual Avatar. The afore mentioned "KINECT" system effectively has two cameras; a traditional VGA color video camera, which takes RGB information from a scene illuminated by a light source 416 and monochrome depth image camera 420 that measures depth, position and motion from the distorted reflections from IR pattern generator/projector 410 IR image(s). "KINECT" imaging system can distinguish between individual persons even if they are partially hidden. Firmware extrapolates what the rest of a person's body is doing as long as it can detect some parts of it. This allows tracking even if the person is standing behind a partially obstructing object. Evaluation of the Avatar's motions when referenced against a dynamic library of known deterministic actions or positions provides a means of classifying particular relevant HCW or patient movements and actions.

The method of operation of the Prime Sense technology for acquiring a depth image is based on light coding. Light coding works by coding the scene volume with near IR light including projecting a composite image comprising a plurality of modulated structured light patterns via IR pattern generator/projector 410 at the room structures and anatomical features of a HCW 600 or patient 920, capturing an image reflected from these surfaces, and recovering pattern information from the reflected image for each modulated structured light pattern using a monochrome depth image camera 420 to read the coded light back from the scene. Pattern information is preferably recovered for each modulated structured light pattern used to create the composite by performing demodulation of the reflected image. Reconstruction of the surface can be accomplished by using depth information from the recovered patterns to produce a depth map. Each signal waveform used for the modulation of a respective structured light pattern is distinct from each of the other signal waveforms structured light patterns of a composite image used for the modulation of the other. The Prime Sense, three dimension image processor 490 executes a sophisticated parallel computational algorithm to decipher the received light coding and produce a depth image of the scene. The processor is capable of combining these decoded images with images acquired from a cooperating VGA color camera 430 improving image resolution, facial recognition and other detection features. Alternately, image detection, identification and tracking may be assisted with added detection capabilities provided by a second set of modulated IR projectors and detectors (440) preferably located on the fixed sanitizer 500.

Figure 6:
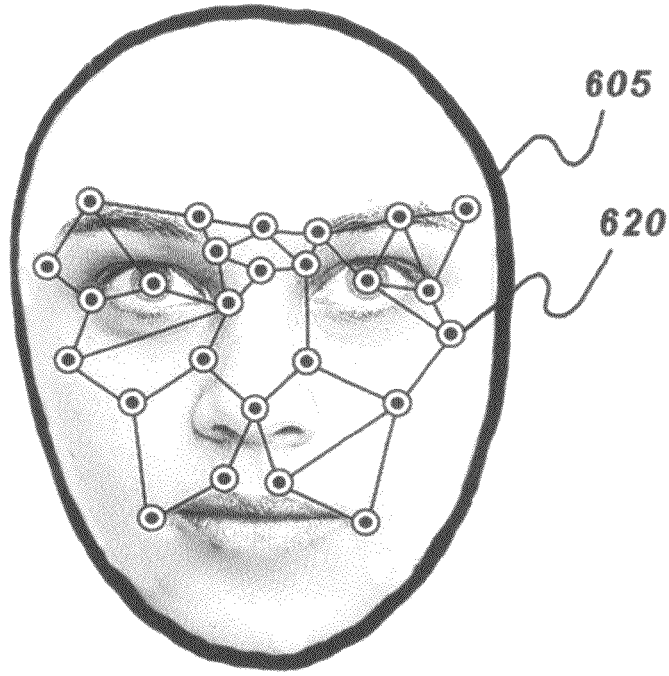
FIG. 6 is a diagrammatic illustration of a computational means of deriving an image value from three dimensional image analysis of the surface of a person's face.
Figure 7:
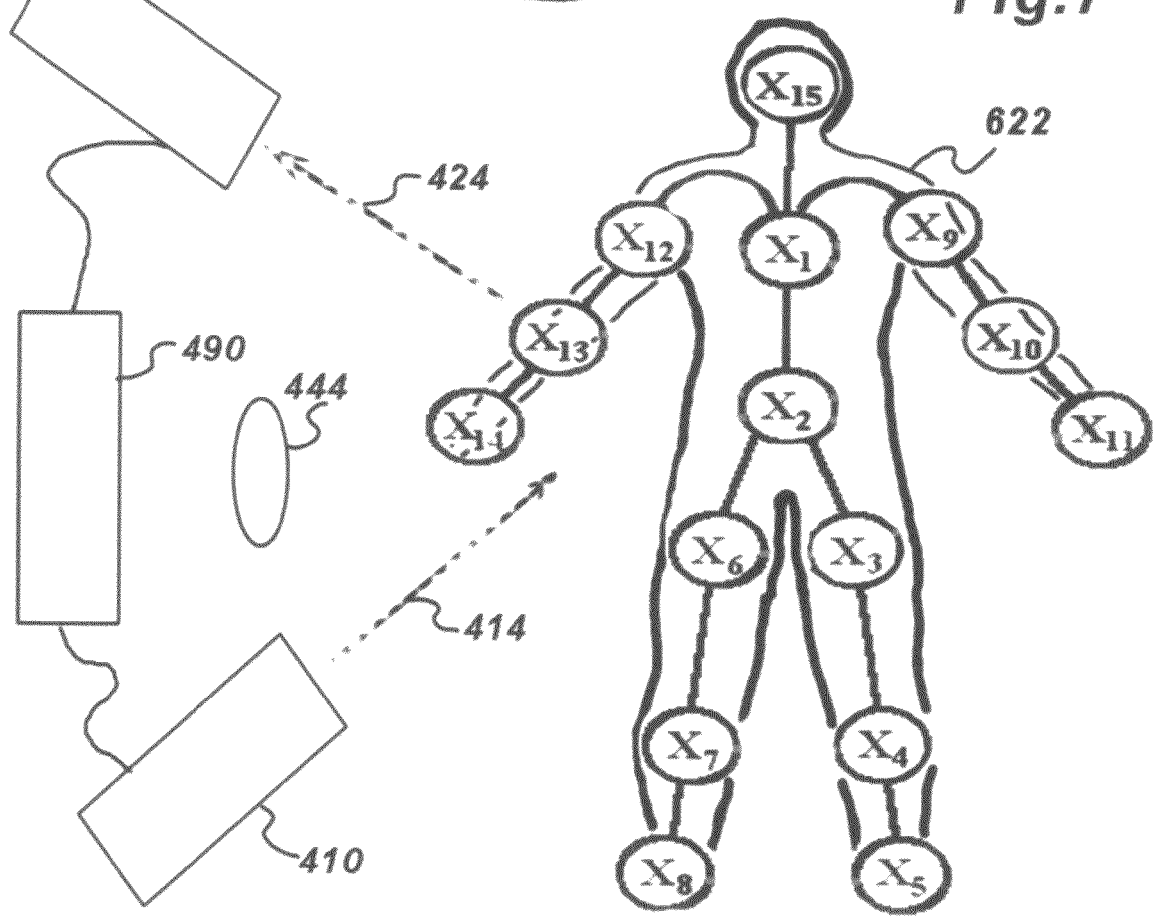
FIG. 7 is a diagrammatic illustration of an electronic and computational means of deriving an image value from three dimensional image analysis of the structure of a subject's body.

FIGS. 6 and 7 provide two views of the derivation of image values 444 from the acquired three dimensional images, parts of which are illustrated diagrammatically. three dimension image processor 490 and system's firmware 492 of three dimensional imaging camera system 440 decodes distortions in a projected IR image 414 generated by infrared pattern generator/projector 410 that is reflected off the scene that includes the HCW, the patient and background and whose reflected images 424 are captured by monochrome depth image camera 420 effectively illustrating three dimensional depth related values {feature vectors} as computational values 620 of subjects body 602. Additional computational algorithms decode the image, thereby generating three dimensional values 622 representing the feature vectors derived from three dimensional images of depth and positioning of a persons body, torso and limbs. {It is important to note that herein, representative three dimensional decoded reflected infrared feature vectors will be referred to as "Image Values 444" in this description for reasons of clarity}. Additionally, these values may then be encrypted for purposes of security (not shown).

Figure 8:
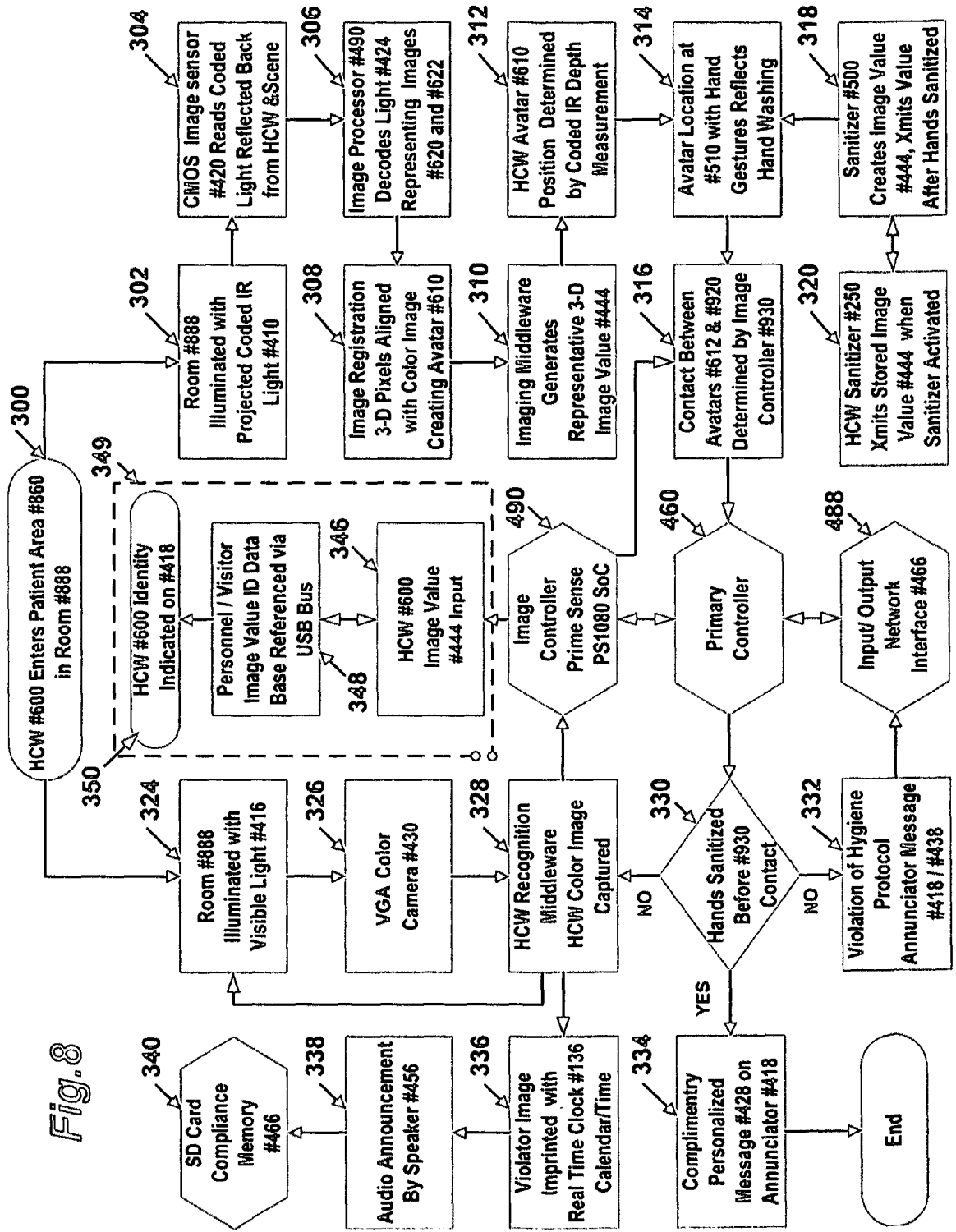
FIG. 8 is a flow diagram illustrating an image capture system and a method for monitoring hand hygiene and patient contact according to various embodiments presented herein.

FIG. 8 is a flow diagram illustrating detection and identification of HCW for tracking and protocol compliance purposes. The process begins with the HCW's entry into the patient's room 300 that is illuminated with projected infrared pattern 302 and visible light 324. The distortion in the reflection of these images provides a means of detecting shape, contour and depth of the image's features 304. The three dimensional protocol monitoring system 100 employs a combination of one or more three dimensional imaging cameras and associated image processing to determine the proximity of a HCW or other person to a patient in multiple increments of increasing or decreasing proximity. The sequence of tracking the HCW 600 by the three dimensional imaging assembly 400 allows the logic incorporated within the three dimension image processor 490 and process controller 492 to ascertain the location, actions and direction of movement of the HCW and respond with the appropriate actions. The significance of such capability is apparent as follows. In steps 306 and 308 the images derived from the reflections of the projected IR image are combined, for additional robustness, with the images derived by RGB camera. This combination of images is processed by the image processor 328 so as to yield computational values 620 of the subject's body 622. In step 310 these values provide a data source for the construction of an image value representative of the three dimensional characteristics of the HCW leading to step 312 and the creation of a representative Avatar 610.

Once the Avatar has been created and tagged with an identifying image value 444 the three dimensional imaging system can readily identify the HCW 600 or Avatars location 316 and actions 314 within the viewing area. Once hand sanitizing has been detected 318 the HCWs image value coding is altered to reflect this change in status 320. Hand sanitizing may consist of actuation of a fixed base sanitizer 500, portable monitor/sanitizer 250 or the detection of hand washing gestures 314 at a sink 510 thereby generating a "Hands Sanitized" signal. The known deterministic three dimensional visual features and gestures of such actions will be recognized by the system's firmware 492 in conjunction with the operating system and hardware of primary controller 460 thereby reflecting a successful hand washing event 330 and generating a favorable compliance report on a remote base 488. Alternately, successful handwashing may be determined by actuation of electrical switches associated with the sink or sanitizers. Upon detection of a person entering the patient's system detection area 888, illumination may be provided 324 to accommodate a VGA color camera 326 capturing the image of a HCW entering the patients care area. Primary controller 360 may then determine if a successful hand sanitizing event has occurred at the appropriate time and location and generate a message on an associated annunciator reflecting same 332/344. Failure to comply with required hygiene protocol will result in the capture and recordation 340 of the violator's image imprinted with a time and date stamp and a verbal warning 338.

Figure 10:
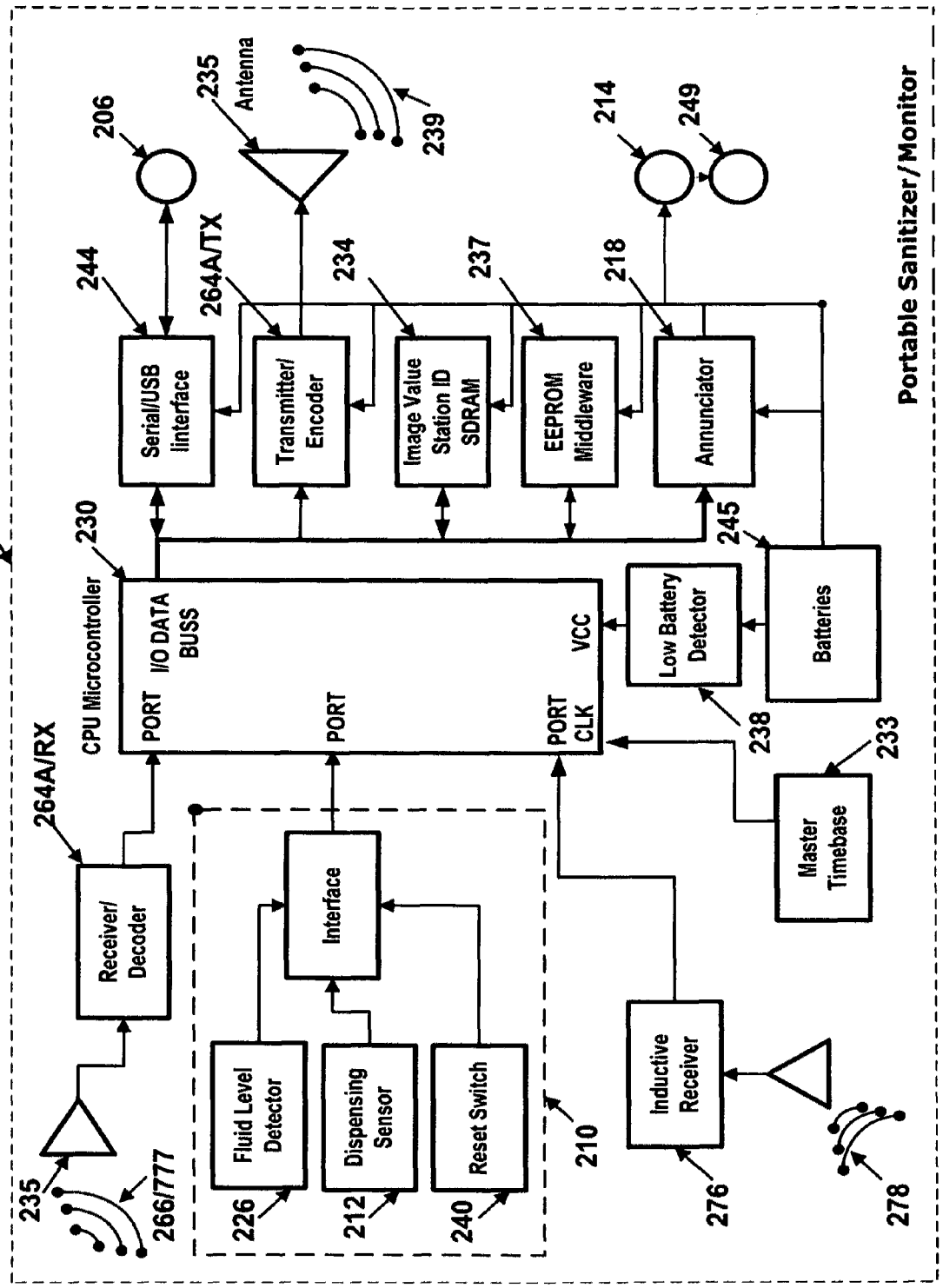
FIG. 10 is a diagrammatic illustration of the portable monitor and a sanitizer/monitor assembly shown in FIGS. 9A and 9B.

FIGS. 9A, 9B an alternative embodiment shown in perspective, of a portable hand sanitizer removably secured to an operatively associated personal monitor as represented in schematic FIG. 10. This portable monitor/sanitizer 250 may be used in place of or in addition to the fixed base sanitizer 500 described in FIG. 14 thereby obviating the need for both. The portable monitor/sanitizer 250 is designed for portability, and could perform both the functions of a wearable monitor 220 and the fixed base sanitizer 500. It could be designed to fit in a pocket or affixed to a belt or other article of clothing. Unlike the fixed base sanitizer 500 described above, the portable monitor/sanitizer 250 would not be associated with a particular room or patient until programmed with a station identifier code 425 via signal 266. A pump-type sanitizer dispenser 210 is shown in the drawings, though other mechanisms for dispensing sanitizing material can alternatively be employed. The sanitizer/monitor assembly includes a battery 245, low battery detector 238 and a activation sensor 212 to detect when sanitizing station identifier code material has been dispensed. This sensor could, for example, detect a change in pressure in the container portion of the sanitizer when the reservoir is squeezed or the pump is actuated. Other features of the portable sanitizer/monitor assembly disclosed herein include a fluid level detector 226, a reset switch 240 and an annunciator 218. The reset switch 240 can be used to override violation warnings and/or messages, but such activation is preferably noted as a violation of hand washing rules and results in the recording of such action in the memory 234 of primary controller 260. The portable sanitizer is preferably employed immediately following detection of HCW in the patient control area 840 by the three dimensional imaging assembly 400 such that its operation is in close proximity to the patient. Actuation of the sanitizer cause associated transceiver 264 RX/TX to generate signal 239. Receipt of signal 239 by the primary controller's transceiver 264RX/TX results in controller 230 generating a "sanitized" message on annunciator 218. Alternately, depending on placement, the fixed base sanitizer 500 may be activated prior to the HCW's entry or exit from the patient control area 840. The portable monitor/sanitizer 250 may include other means of communicating such as a warning mechanisms i.e. flashing LED 214 or speaker 249 are preferably designed to avoid disturbing a sleeping or resting patient while providing adequate prompting to the health care worker to wash his hands. The three dimensional protocol monitoring system 100's distance resolution monitoring capabilities, including portable monitor/sanitizer 250 and fine location determination capabilities of the three dimensional imaging assembly 400 may be utilized to ensure the health care worker be in patient care area 840 in close proximity to the patient when requested to sanitize his/her hands by annunciator(s) 218/418 thereby assuring minimal opportunity for HCW or patient contamination subsequent to hand sanitizing. Alternately, the sanitizer dispenser 210 may be removably secured to the portable monitor/sanitizer 250 thereby allowing the wearable monitor 220 to perform only the functions of a portable HCW/visitor monitor as required.

The monitor may be programmed to be responsive to station ID clearing signal 777 from the contaminated area reset transmitter 724, receipt of such signal upon room entry or exit would cause the associated displays to indicate a contaminated status. Alternately, station ID clearing signal 777 emitted contaminated area reset transmitter 724 may be generated by transceiver 264 integrated into the fixed base sanitizer 500 or the three dimensional imaging assembly 400. If the portable sanitizer is actuated following the worker being detected in patient control area 860, the status is changed to uncontaminated and an appropriate signal is sent to the primary controller 460. If the worker has not sanitized his hands, the status will remain "contaminated" and a violation may be noted if he/she is detected in closer proximity to the patient 920 in patient care area 840. The portable monitor/sanitizer 250 is capable of being programmed with the identifying image value 444 associated with the Avatar carrying said monitor/sanitizer. It should be appreciated that this scheme for remotely monitoring activity of a portable sanitizer differs greatly from previous art including RFID schemes in that the proposed monitor associated with the sanitizer has no personality or identity (identifying coding) until it is remotely "re-programmed" with a unique image value 444 reflecting the appearance of the bearer. This capability allows for sharing or for simplifying the distribution of sanitizers within a hospital environment e.g. all portable sanitizer/monitors can collectively be filled at the end of the day without concern for "whose" sanitizer belongs to whom when redistributed to personnel.

FIG. 10 schematically shows the operation of the wearable monitor 220 and the portable monitor/sanitizer 250. The wearable monitor 220 would have the same configuration and capabilities as the HCW sanitizer/monitor combination assembly and be programmable in the same manner but would not necessarily include a sanitizer dispenser 210 and it's operatively associated components to include fluid level detector 226, dispensing sensor 212, and reset switch 240. The independent monitor or its related configuration as sanitizer/monitor assembly can be affixed to a chain or cord (not shown) and worn around the neck and/or include a clip (not shown) for fastening it to the visitor's clothing. Most described elements are common to the HCW portable monitor/sanitizer 250 and the wearable monitor 220 including battery 245, low battery detector 238 associated interfaces to CPU microcontroller 230, master time base 233 a central processing unit 230, an operating system located in memory 237, a re-writable memory 234 for storing image values 444, station identifier code 425 and logic levels, an LCD annunciator display 218, a LED display 214, a speaker 249, a transceiver 264A TX/RX for transmitting and receiving information via signals 239/266 from the transceiver 264 operatively associated with primary controller 460. The tracked HCW's Avatar 612 image identifier values 444, station identifier code 425 and logic levels are programmed into the personality free monitor's memory via a low power inductive signal 278 transmitted by primary and/or sanitizer transmitter 274 and received by integral low power receiver 276 operatively associated with the monitor's CPU microcontroller 230. Do to the short effective transmission range of said signal (less than 1 meter), the association of the transmitted signal 278 with the targeted monitor receiver assures a positive and reliable correlation between the monitor's identification codes and the image of the concurrently visualized HCW detected in an associated proximate finite area while bearing said receiver. This action is accomplished automatically upon initial detection of a HCW bearing said monitor entering a finite imaging and monitoring area of three dimensional IR imaging device 440 thereby causing the primary controller 460 to initiate the sending of a station ID clearing signal 777 and subsequently a station identifier code 425 followed by an identifying image value via data signal 239 to transmitter 274. This receipt of this signal causes a message to be generated on the LCD display 218 associated with the wearable monitor 220. A warning or other alert could be similarly displayed on the annunciator 418 associated with the primary controller 460. To provide a means of prompting and thereby assuring activation of the portable sanitizer at an appropriate distance from the patient, operating system logic in middleware located in memory 237 of the portable monitor/sanitizer 250 associated with CPU 230 may be provided to preclude the generation of a portable dispenser activation signal 239 by the sanitizer back to the primary controller, prior to receipt of a location dependent monitor activation signal 266 from the primary controller operated transceiver 264. Alternately, pre-programming the monitor with a definitive identification code representing the HCW' image may be accomplished by programming the middleware memory 237 with the tracked HCW Avatar 612 image identifier values 444 and placing the associated station identifier code 425 into portable monitor's memory 234. This may be accomplished via connection to fixed base sanitizer 500's serial port 566 or system data interface 462 via monitor's serial port 206 operatively associated with data buss 244.

Figure 11:
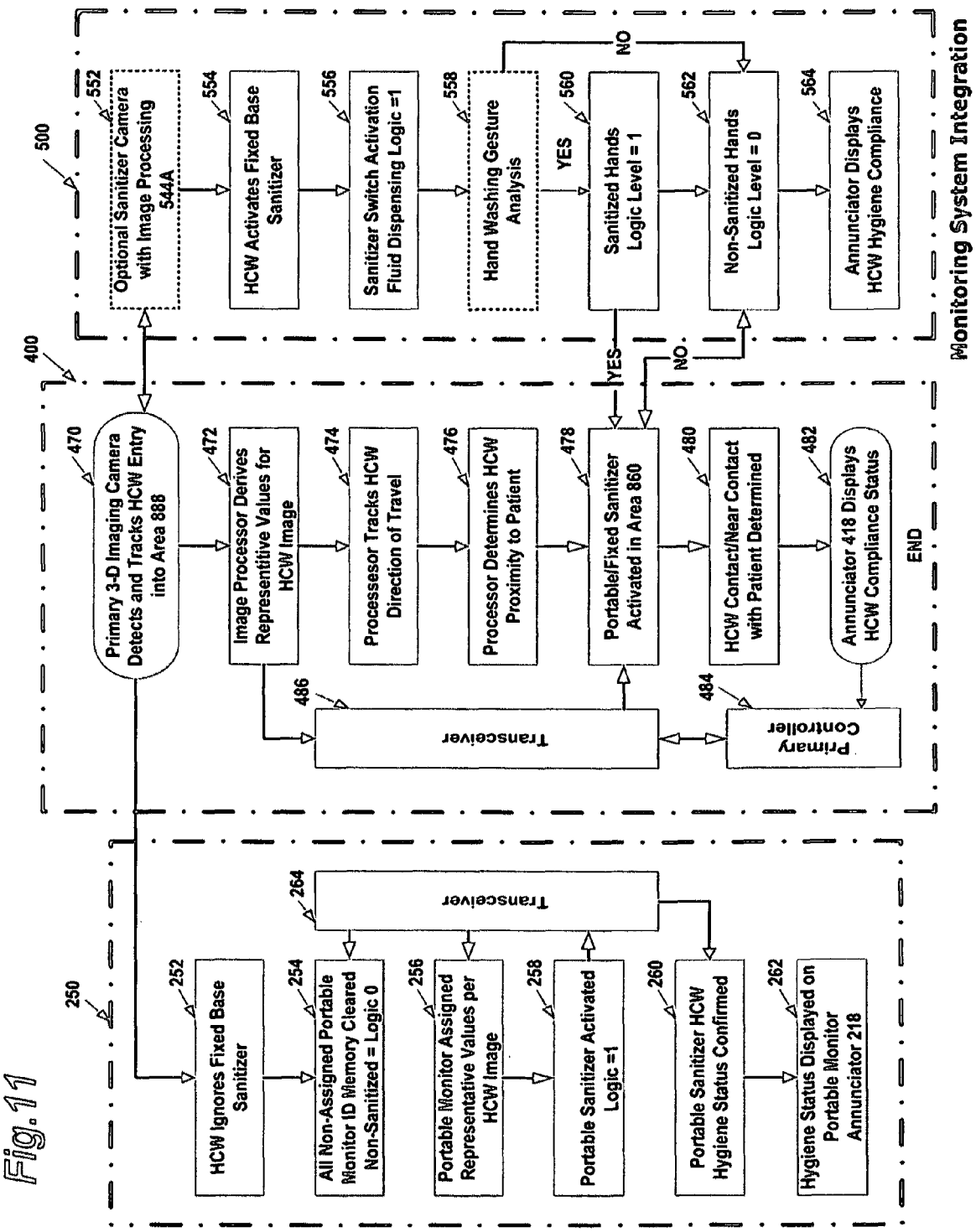
FIG. 11 is a flow diagram of the three dimensional imaging system, sanitizer, portable sanitizer and monitor comprising three dimensional protocol monitoring system 100.

FIG. 11 is a diagram reflecting the operative interaction between the three dimensional IR imaging device, the fixed base sanitizer and the wearable monitor, all of which comprise the three dimensional protocol monitoring system. The HCW enters the perspective viewing area of the three dimensional imaging system 470. The captured three dimensional images are processed by the image processor, generating an Avatar of the HCW and assigning an identifying image value derived from three dimensional features of the subject HCW 472. The image processor and support circuitry tracks the direction of travel and the absolute location of the HCW 474 relative to the patient and associated sanitizer within the patient's room. The aforementioned imaging system is configured in such a manner as to be capable of viewing and discerning all persons within its field of view while internal computational logic is capable of determining the HCW's proximity to the patient 476 via visual cues and distance determination algorithms. Per requisite protocol, the HCW may stop at the system associated fixed base sanitizer. The fixed base sanitizer may include an optional three dimensional infrared imaging device as described supra, that works cooperatively with the imaging system associated with the primary controller 552. Activation and dispensing of sanitizing fluid from the fixed base sanitizer 554 causes primary controller to generate a logic #1 associated with Avatar identified with image value indicating HCW is sanitized 556. Alternately, sanitizer transmits three dimensional image value representative of detected HCW and a logic #1 to primary controller as illustrated in step 552. Interpretation of deterministic kinetic algorithms of hand movements detected by one or more of the associated cameras may be utilized to determine hand washing at a sink 558 or fixed base sanitizer.

If the HCW fails to implement either of these hand washing routines, default value logic #0, 562 is assigned to the HCW image. If hand sanitizing compliance is accomplished, a logic #1 560 is assigned to the HCW image and the results are displayed on the systems cooperating annunciators 564. The primary controller assembly is operatively associated with the image processor and is capable of receiving a signal indicative of the appropriate activation of an associated sanitizing device 478. Once a particular distance more distant from the patient, patient control area and subsequently, a closer distance, patient care area (arms length) between patient and HCW is determined the annunciator(s) will display a message associated with the relative distance and the hygiene status of the HCW 482. Visual computational and deterministic actions of the HCW are observed and interpreted by the system's firmware 492. When visual cues from a combination of particular kinematic hand movements and distances between patient and HCW are referenced by the image controller middleware against a programmable pre-established deterministic data base, HCW patient contact may be inferred 480. A third method for the HCW to satisfactorily complying with requisite hand hygiene protocol is via the utilization of a portable monitor/sanitizer 250. If the HCW has ignored the prior methods of sanitizing their hands 252 they still have an opportunity be in compliance with hygiene protocol by activating a portable sanitizer they are wearing. The means of securing said sanitizer/monitor may be varied and include a belt clip, lanyard, pocket clip or simply held in one's hand. Unlike RFD transponder tracking, the transceiver that is incorporated herein is not required to locate the HCW. The portable sanitizer/monitor may be cleared of all information upon receipt of a low power signal that may be generated by transceiver associated with the primary controller upon detection of the HCW in system detection area, which would cause the resetting of all registers in the monitor to a default logic #0 upon a worker entering or leaving the contaminated area step 254. Alternately, periodically, the memory in all non-assigned (not programmed with image value and station value) monitors within the patients room maybe cleared (reset to default logic #0) when the transceiver 264 in the monitor receives a low power signal from the transceiver associated with the primary controller 254. Optionally, the memory of all non-programmed monitors may be programmed to automatically default to logic #0 after a fixed period of time has elapsed since sanitizing has last been accomplished. Imaging information including HCW image values relating to a specific Avatar is generated by the image processor. Included in this information may be a station identifier code which is a specific coded identifier uniquely associated with a particular primary controller. The purpose of this configuration is to be sure that the indicated sanitized status of a HCW cannot be carried from patient care area to another monitored patient care area, thereby precluding the possibility of cross contamination between patients.

Upon initial detection in system detection area, the image value associated with the particular HCW's image is transmitted to the HCW's co-located monitor 256, thereby giving the monitor an electronic personality that is similar or identical to the image value as is associated with the HCW's tracked image (Avatar). The identification numbers (image value) for the person carrying the monitor must objectively match those programmed into the sanitizer/monitor in order for the primary controller to indicate satisfactory sanitizer activation. This arrangement assures that the system is able to identify a particular portable sanitizer/monitor activity as well as the hygiene status of the HCW once the sanitizer is activated as it is directly associated with the image of the HCW carrier thereby creating a generic sanitizer/monitor that contains no pre-established coding and can be sourced from a pool of sanitizer/monitors. The advantage of this arrangement becomes obvious as filling, servicing, storage or replacement of this item may be accomplished with the HCW no longer having to identify "their" uniquely pre-programmed sanitizer/monitor containing an identifier code previously associated with the particular HCW before its actual use. Additionally, in the use of a pre-programmed monitor/sanitizer for security purposes, the possibility for a HCW to falsely represent themselves as someone else by the use of someone else's identifying ID monitor/sanitizer is no longer practical as the image contained within the once programmed monitor can only be used with the person whose image value matches the image value determined by the three dimensional protocol monitoring system 100. Upon initial detection, when entering a monitored area, a lack of correlation between the ID image value contained within the monitor and the image value derived from observation of the HCW by the three dimensional protocol monitoring system would be a cause for an alarm to be indicated. Activation of the sanitizer causes the cooperating monitor to transmit a unique image value associated with that particular HCW, thereby creating a logic #1 within the system 258. This logic value is associated with the image value of the HCW being tracked by three dimensional protocol monitoring system, as described previously, with the activation of the fixed base sanitizer. Transceiver 264 then receives a confirmation message indicating hygiene protocol compliance or lack thereof from the primary controller's 260 transceiver 486 subsequently displayed on the monitors annunciator 262. The manner in which the elements described above relate to each other is generally represented in the schematic shown. Two types of sanitizers, portable monitor/sanitizer 250 and fixed base sanitizer 500 are shown in the figure. While both stationary and portable sanitizers can be incorporated within the three dimensional protocol monitoring system 100, only one type is necessary. If two types are used, they should be programmed so that they function in a complementary manner.

Figure 12:
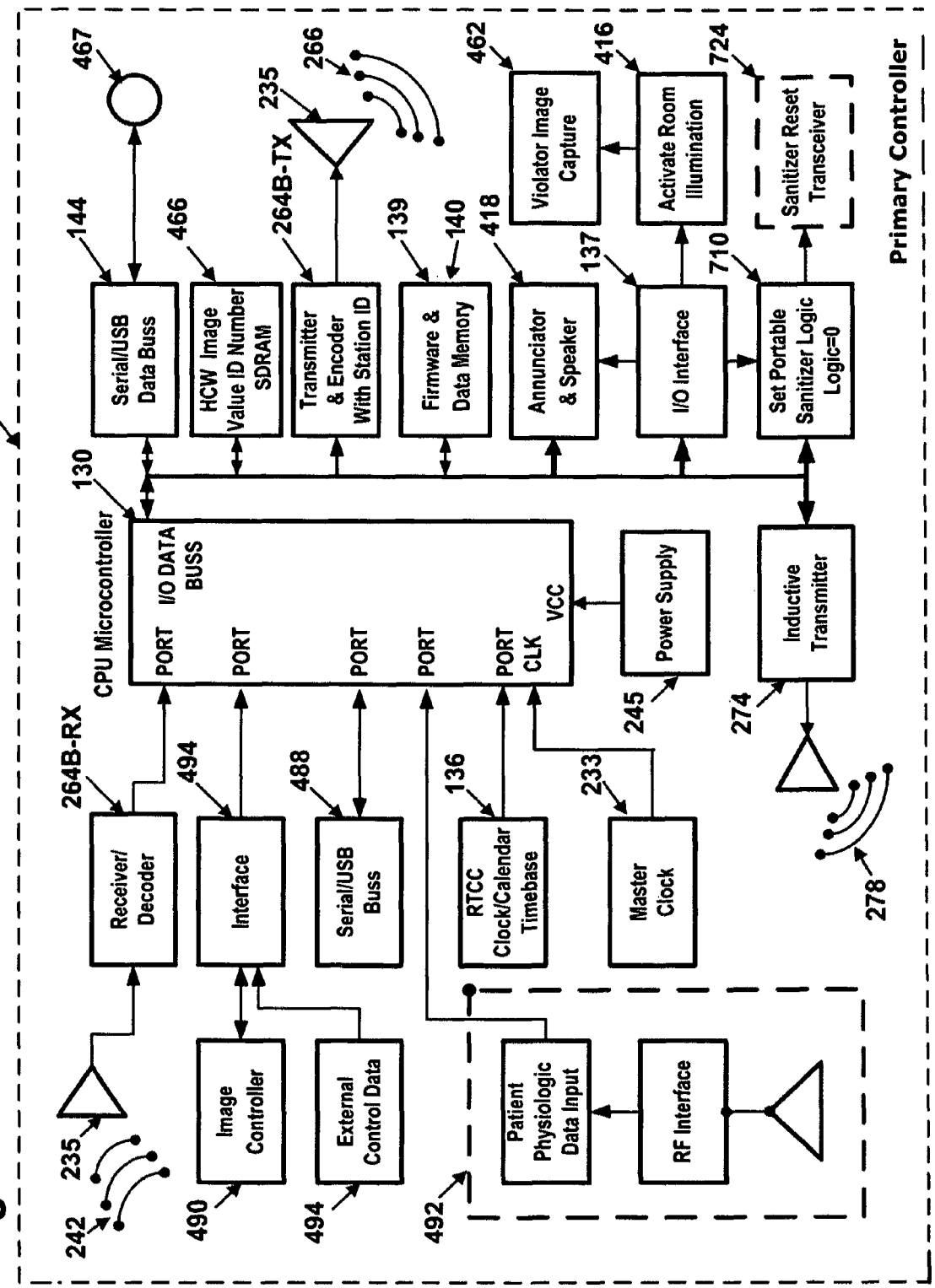
FIG. 12 is a schematic illustration of a primary controller usable with a three dimensional protocol monitoring system 100.

FIG. 12 details a schematic of components comprising the primary controller 460. It will be appreciated that some redundancy is built into the elements of the system described herein, which is preferred but is not considered essential. The annunciator 418 may be an LCD display prominently displayed in the patient's room capable of displaying graphics with alphanumeric and text characters. It is contemplated this annunciator is capable of alerting the HCW 600 in the event it is determined that the worker is not in compliance with the institution's hand washing protocol. Information relating to hospital rule compliance and the patient's conditions and requirements may be provided to the HCW via this annunciator and associated I/O interface 137 and CPU microcontroller 130 configured to receive information or instructions from integrated and remote hardware and to cause the operation of other integral or remote devices. Inclusively, it is anticipated the annunciator 418 will have the capabilities to display physiologic information 429 from one or more patient's physiological monitoring devices, such as a data derived from a pulse-oximeter, EKG or similar monitoring device whose parameters are accessed via wired or wireless means.

Additionally, provisions may be made for the annunciator to access and display patient's electronic health records stored locally on the fixed or removable memory 466 and/or from a remote data base. Such remote patient record information may be accessed by the primary controller via the included system data interface 462 operatively associated with serial data buss 144 or the included wireless transceiver 264RX-TX. The fixed or removable memory 466 which may be programmed remotely may be used to store pertinent patient data such as the patient's name, drug allergies, special care needs and/or other patient-specific information, any or all of which can be displayed on the annunciator 418. A speaker 456 associated with the annunciator is also provided. A three dimension image processor 490 is coupled to the CPU by an interface 494 via 144. The primary controller 460 is capable of wirelessly communicating HCW image value and logic status as well as station ID data via encoded signals 266/239 with the fixed base sanitizer transceiver through the use of transceiver 264RX/TX and antenna 235. Additionally, the primary controller may communicate HCW image, logic and station ID values to a proximate portable monitor/sanitizer via encoded signal 278 generated by a transmitter 274 or alternately through system data interface 462 operatively associated with serial buss 144. three dimension image processor 490 and patient data on fixed or removable memory 466 communicates with CPU 130 via a control buss 494 and bi-directional buss 488 or wirelessly through transceiver 264RX/TX. CPU associated firmware in data memory 139 or fixed or removable memory 466 may be accessed via serial buss 144 through USB connector 467. The primary controller 460 includes a CPU microcontroller 130 that is operated by one or more power supplies 245. The CPU microcontroller 130 is employed for executing stored instructions. A data memory 139 stores operating instructions which can be retrieved and executed by the microcontroller. The master time base 233 provides machine cycles for the microcontroller and watchdog timers. A real time clock calendar (RTCC) 136 provides time and date stamp information to the microcontroller for documenting health care worker actions and/or violations. A fixed or removable memory 466 such as an DRAM or SD memory card, is capable of storing information, that must be retained if the power source is interrupted, such as patient related information, protocol violations and the violator's image value ID and RTCC stamp. I/O interface 137 communicates logic levels of HCW hygiene status 710 to memories of sanitizers and monitors via 264TX or contaminated area reset transmitter 724 while light source 416 with capture of a violators image via system data interface 462.

Figure 13:
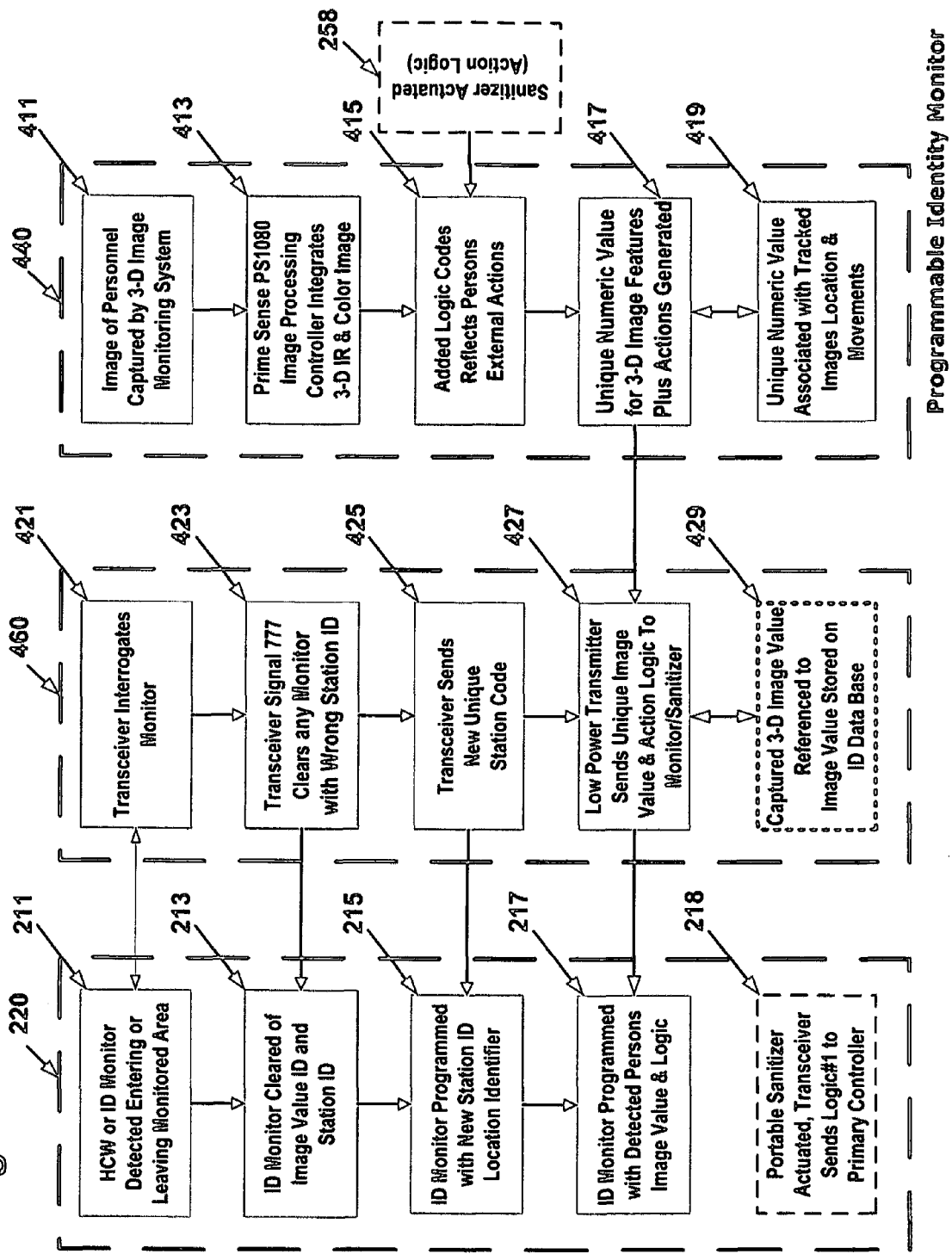
FIG. 13 is a flow diagram of a programmable identity monitor usable with or without a portable sanitizer and incorporated within a three dimensional protocol monitoring system 100.

FIG. 13 is a flow diagram representing the implementation of a portable monitor operatively associated with three dimensional protocol monitoring system 100. The monitor may be provided with or without an associated portable sanitizer. The programmable wearable monitor 220 provides an electronic, passive, non-invasive, means of identifying both a HCW and their operatively associated portable monitor/sanitizer 250. A three dimensional IR imaging device capable of detecting and processing characteristics and physical motions, locations and distance derived from video images of a scene that includes a human form. Persons entering a patient's room 411 are initially detected by one or more cameras associated with a three dimensional imaging system. The image processor integrates the images captured by the camera(s) into a cohesive digital form 413. A logic value is assigned to the captured image 415 reflective of an external action or data input such as 258. The captured image(s) is processed by an image processor in a manner so as to derive 3 dimensional features of the image which may include depth and dimensional surface characteristics derived from feature vectors of the subject. The image of the person detected in the scene is then assigned an image value based on a plurality of observable characteristics shown in (FIGS. 6/7) 417.

The HCW's location relative to the patient is visually tracked and direction of travel plotted while their physical form and actions are represented in three dimensions by analysis of feature vectors or a representative Avatar whose identity is previously assigned as an image value 444. A transceiver associated with the image processor and a primary controller 460 interrogates the monitor 421 entering the room and determines if the monitors stored image value matches the image value derived by observation of the person by the three dimensional image processing assembly. A match of image values by the monitoring system allows the person bearing this particular monitor to proceed to an allotted location for accessing additional logic levels. Alternately, upon initial visual detection by the three dimensional IR imaging device 440; the primary controller's associated transceiver sends a low power station ID clearing signal 777 clearing image value data while transferring the time stamp station codes 215 associated with that particular three dimensional imaging assembly 423. This memory clearing reset action functions in a manner as to avoid the bearer of the portable monitor transitioning from one patient control area to another, thereby cross contaminating patients while carrying an identity which may falsely represents the bearer and/or a hygiene status which may no longer be valid. Such situation may be presented where the HCW may have left one patients room for another or the situation where there may be more than one patient and more than one patient associated monitoring system sharing a room. Upon subsequent or concurrent detection of the person bearing the monitor by the imaging assembly the primary controller associated transmitter then transmits a unique station identifier code 425 which is received by the now identity less monitor effectively reprogramming it with the new station identifier code 215, thereby developing an exclusive communication handshake between that particular imaging assembly and that particular monitor. Primary controller 460 concurrently causes the sending of a signal a low power signal from transmitter 274 containing information regarding aforementioned image value and logic value 427 to the proximate monitor thereby associating this particular monitor's identifying image value code and logic level 217 with the image value (identity code) and/or logic level of the HCW bearing said monitor currently being observed by the imaging system. The subsequently activation of the sanitizer 218 will cause a change of logic value for the monitor and associated HCW. This change in status will be transmitted to the primary controller's transceiver by the monitor's transceiver thereby causing the associated HCW's logic status to change to logic #1 within the controller and to be stored in primary controller memory while the sanitized status is displayed on one or more annunciators. Alternately, if required, additional information relating to the associated person's identity value and logic level may be wired or wirelessly acquired by the primary controller referencing a conforming external data base 429.

Figure 1:
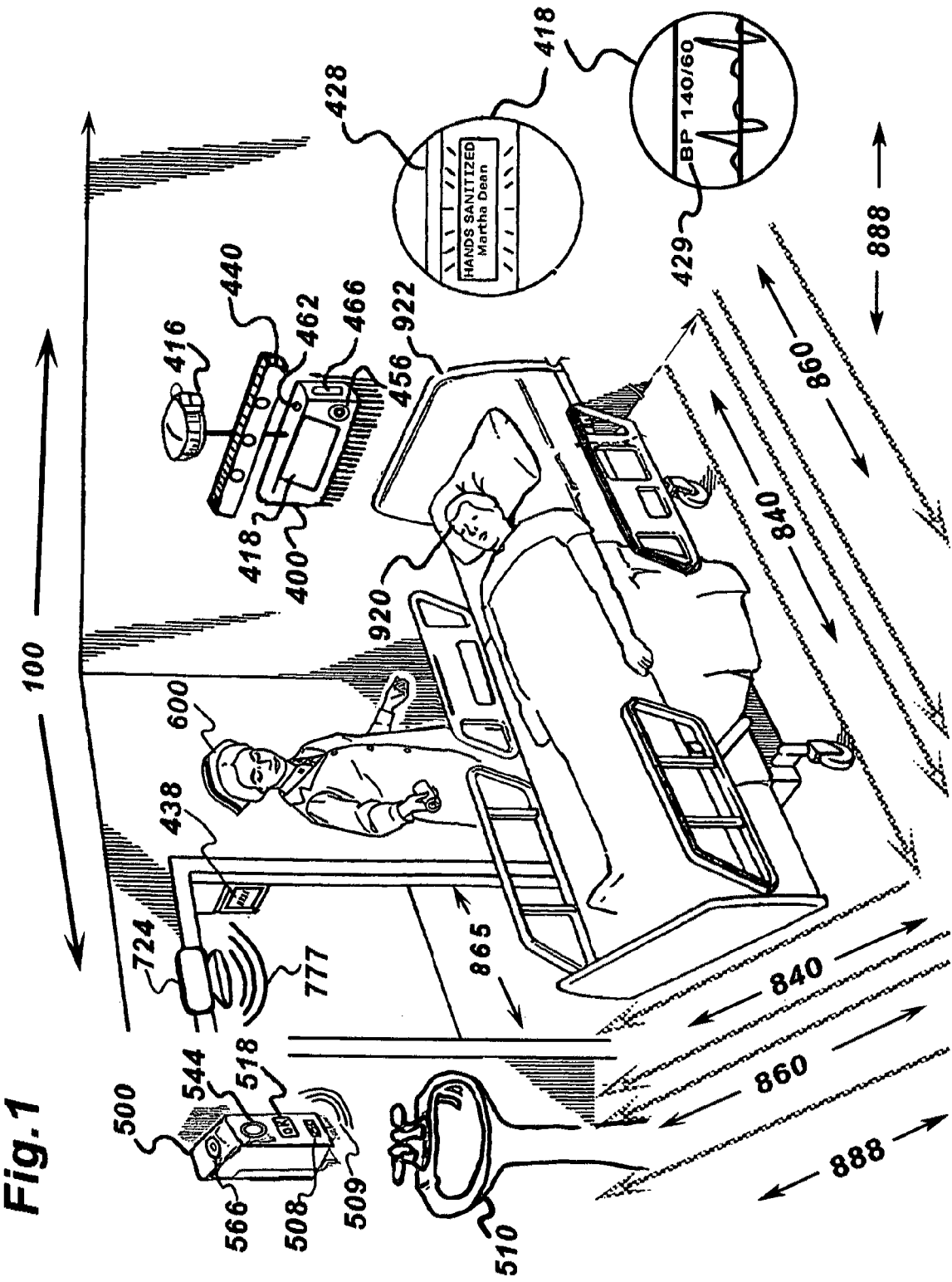
FIG. 1 is a perspective view showing a hospital room, a patient, a Health Care Worker and a hygiene monitoring system in accordance with the invention.
Figure 2:
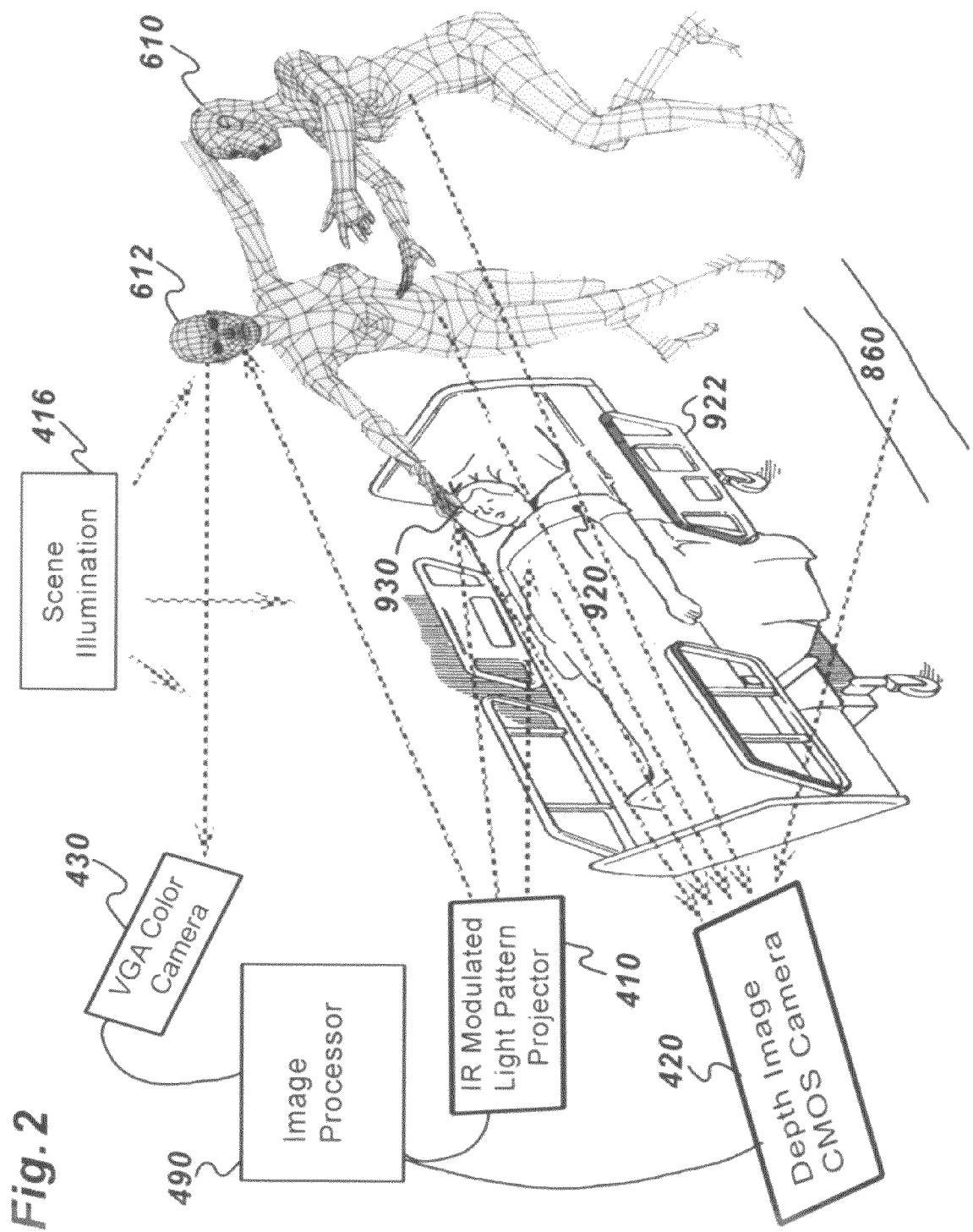
FIG. 2 is a perspective view of a three dimensional imaging and monitoring system capturing the image of a patient and proximity of a HCW to a patient as an Avatar.
Figure 3:
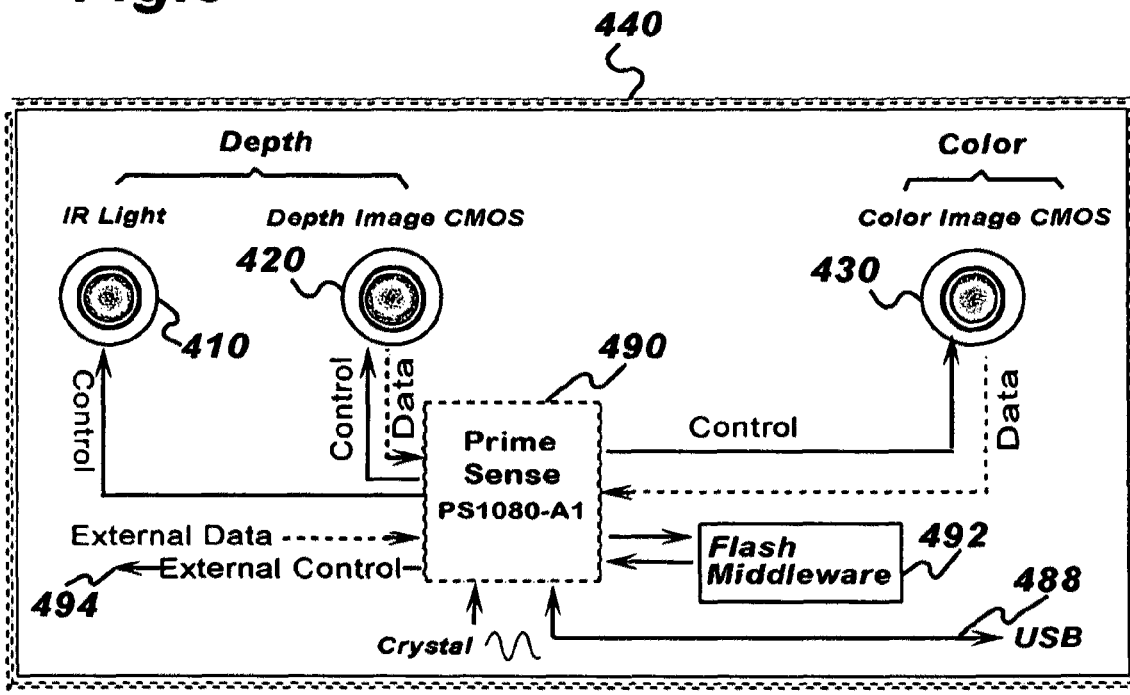
FIG. 3 is a diagrammatic illustration of the components of a three dimensional imaging system.
Figure 14:
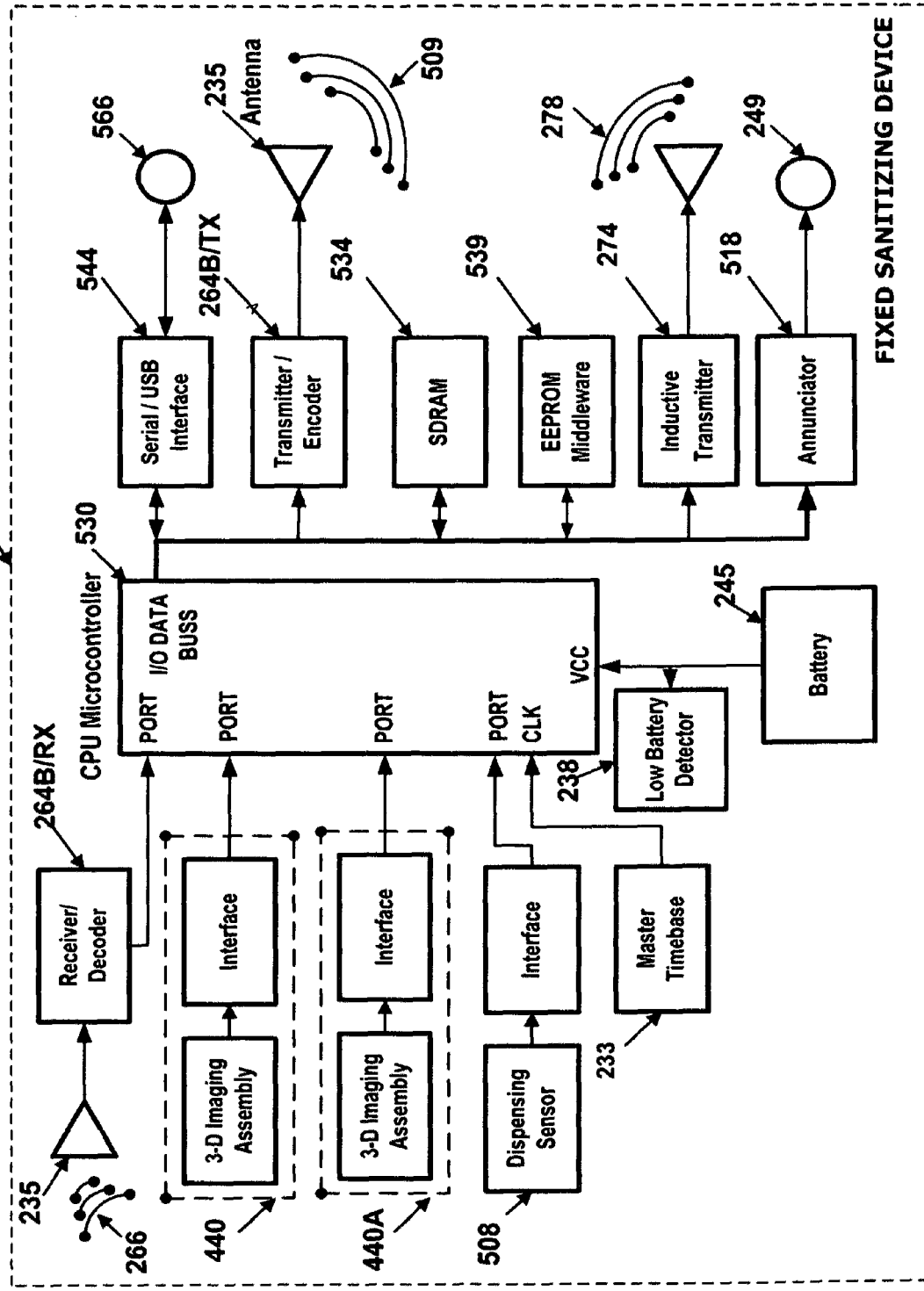
FIG. 14 is a schematic diagram of a fixed base sanitizer usable within a three dimensional protocol monitoring system 100.

FIG. 14 is an illustrative schematic diagram of the fixed base sanitizer 500 employed in the three dimensional monitoring system shown in FIG. 1. The sanitizing dispenser may function as a primary or as a supplemental image detection means by inclusion of a three dimensional IR imaging device 440A such that the image of the HCW 600 may be captured and processed as above, thereby creating an Avatar 612 with an associated image value 444 which then, wired or wirelessly, communicates with the primary controller of the three dimensional protocol monitoring system 100. The transceiver 264A associated with the sanitizer is preferably programmed with a discrete code associated with a particular patient, a patient care area contained within system detection area 888, or a patient's room or support apparatus. Utilization of the sanitizer as indicated by activation of sanitizing sensor 508 will cause the generation of a signal by transceiver 264A controlled by CPU microcontroller 530. This action results in the antenna 235 associated with the transceiver 264RX/TX transmitting an encoded compliance signal 509 that is received by the primary controller's transceiver. Information contained within this encoded compliance signal 509 includes the assigned discrete station code of the originating sanitizer along with an imaging value 444 and the hygiene logic value of the HCW indicating their hygiene status i.e. successful activation of the sanitizer. Image value 444 is derived from co-operating three dimensional imaging assembly 440 or co-located imaging assembly 440A configured to viewing HCW sanitizing actions at fixed base sanitizer 500 or sink 510. Concurrently, similar information may be shared with the portable monitor/sanitizer receiver 276 via a low power signal 278 forwarded by transmitter 274 or via data port 566 associated with serial data buss 544. The logical operations of the sanitizer are controlled by an integral CPU microcontroller 530 powered by a battery 245 monitored by a low battery detector 238. Data communication amongst co-operating support system components such as operational firmware in memory 539, image values, station codes, violation images and operational statistics relating to the use of the sanitizer stored in re-writable memory 534 and information for display by annunciator 518 and speaker 249 are communicated along serial data buss 544 which is externally accessible via USB port 566. As discussed hereafter, the worker must preferably use a hand sanitizer associated with the patient or room in order to avoid a warning signal when contacting the patient. The electronic sanitizing sensor 508 may be an infrared or proximity sensor that, in addition to causing the generation of the encoded compliance signal 509, also causes soap or other sanitizing material to be dispensed. It can alternatively be associated with a mechanical lever (not shown) that causes the compression of the soap-containing bag. The fixed base sanitizer 500 further includes a receiver decoder 264A/RX with an associated antenna 235. This enables the sanitizer to receive encoded signals from the three dimensional imaging assembly 400A or alternately three dimensional IR imaging device 440 via primary controller 460 that will cause the annunciator 518 on the sanitizer to display the current hygiene status of the HCW while acknowledging receipt of the transmission and optionally, provide identifying information regarding the health care worker. In this manner, the primary controller 460 may integrate the information regarding the hand washing activity of the health care worker along with an identifying image value 444 and the HCW's location and actions derived from the three dimensional IR imaging device 440. The system accordingly tracks whether persons wash their hands using particular, patient-associated sanitizers and updates protocol compliance information stored in fixed or removable memory operatively associated with the primary controller.

Figure 15:
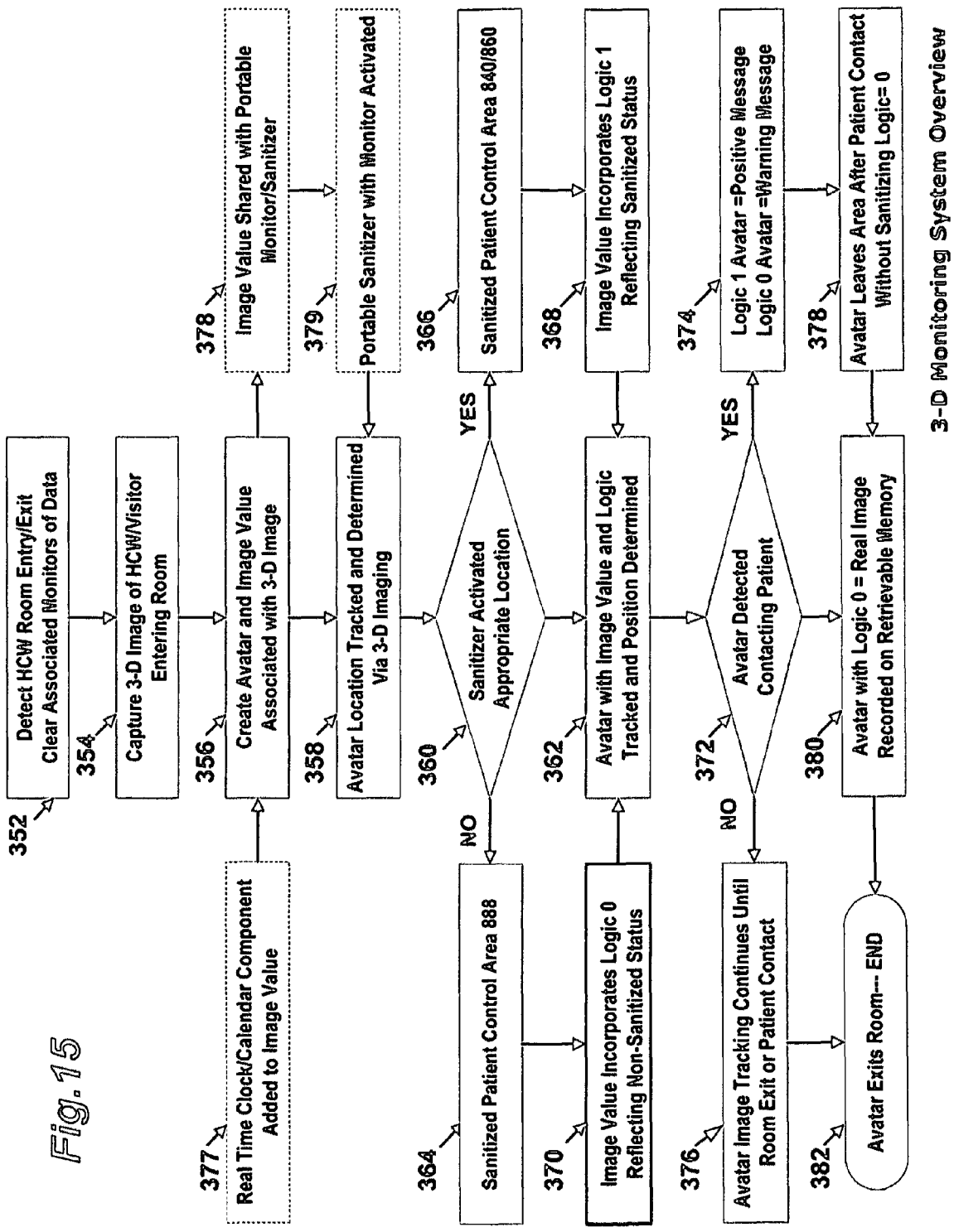
FIG. 15 is a flow diagram illustrating a three dimensional imaging system and method for monitoring and tracking a HCW/visitors proximity to a patient in a patients room, programming an associated monitor and monitoring the HCW/visitor's use of a fixed and/or portable hand sanitizing device according to various embodiments presented herein.

FIG. 15 is a flow chart illustrating the operation of the three dimensional protocol monitoring system 100 as shown. The elements of the system are designed to passively identify HCW's caregivers and visitors without the assistance of badges and determine their hygiene status and whether institutional hand washing protocols have been followed, and to cause selected signals to be generated and certain information recorded depending on whether a health care worker or other persons has been compliant with required protocol. Various situations may occur, which will cause the system to react in different ways. A Health Care Worker is detected initially entering a patient's room via a three dimensional imaging system capable of detecting and determining the human form within a scene. Though a portable ID monitor is not required for the proper operation of the monitoring system, if such a monitor is present, detection of persons entering or exiting patient's room may result in the clearing of all identifying information associated with such monitor 352. The aforementioned imaging system then captures via one or more three dimensional imaging cameras, a three dimensional image of the person entering the room 354. Computational image processing, utilizing captured three dimensional images, then creates a representative image value derived from feature vectors that is then associated with a representative Avatar derived from the three dimensional characteristics of the observed individual 356. A time stamp including date and station location may be added or incorporated into this image value 377. Optionally, if an operationally associated portable sanitizer is incorporated into the monitoring system, the aforementioned image value is transferred via a signal that is shared via wireless means with a portable monitor carried by the tracked individual 378. The representative Avatar, encoded with a unique identifier (image value), is then tracked and its relative position to the patient or the patient's support apparatus is determined 358. The Avatar's location and subsequent sanitizing activity, determined by a signal generated by the activation of a portable sanitizer associated with a particular person's Avatar and their monitor 379 or activation of an operatively associated sanitizer associated with a particular location within the patient's room causes a logic signal to be generated that reflects the hygiene status of that individual Avatar 360. If the fixed or portable sanitizer operatively associated with a monitor is activated by an Avatar at an acceptable time or location 366 per protocol requirements, a logic value (logic #1) is associated with that particular Avatar's image value 368. Conversely, if the individual (Avatar) fails to sanitize at the appropriate time or location 364 a logic level value (logic level #0) is assigned to the representative image value 370. The representative Avatar's movement and location continues to be tracked and their relative position and proximity to the patient is determined 362 on an intermittent or continuous basis. Detection of the Avatar in zone #1 (patient control area more distant from patient) will result is a message reflective of that particular patient proximity and HCW's hygiene status and protocol compliance, Detection in zone #2 (patient care area 840 closer to the patient) results in an alternate, perhaps more compelling message, corresponding to their closer proximity to the patient and the HCW's hygiene status and protocol compliance. Contact with the patient, as observed by the system's camera(s) and the associated image processing algorithms regarding the HCW's proximity to the patient and/or specific deterministic actions visually detected as performed by the HCW, will be reflected in associated annunciator messages whose content 374 will be determined by the hygiene status of the HCW prior to time of detected patient contact 372 and subsequent to patient contact by the HCW, upon entry into system detection area 378. Systematic determination of failure to comply with hospital hygiene protocol regarding patient contact will cause the activation of room illumination and the recordation of the real-time (true) image of the protocol violator and which image will be stored in the monitoring systems memory for administrative action 380. Representative Avatar location tracking and behavioral action monitoring continues 376 until Avatar exits patients room 382.

Figure 16:
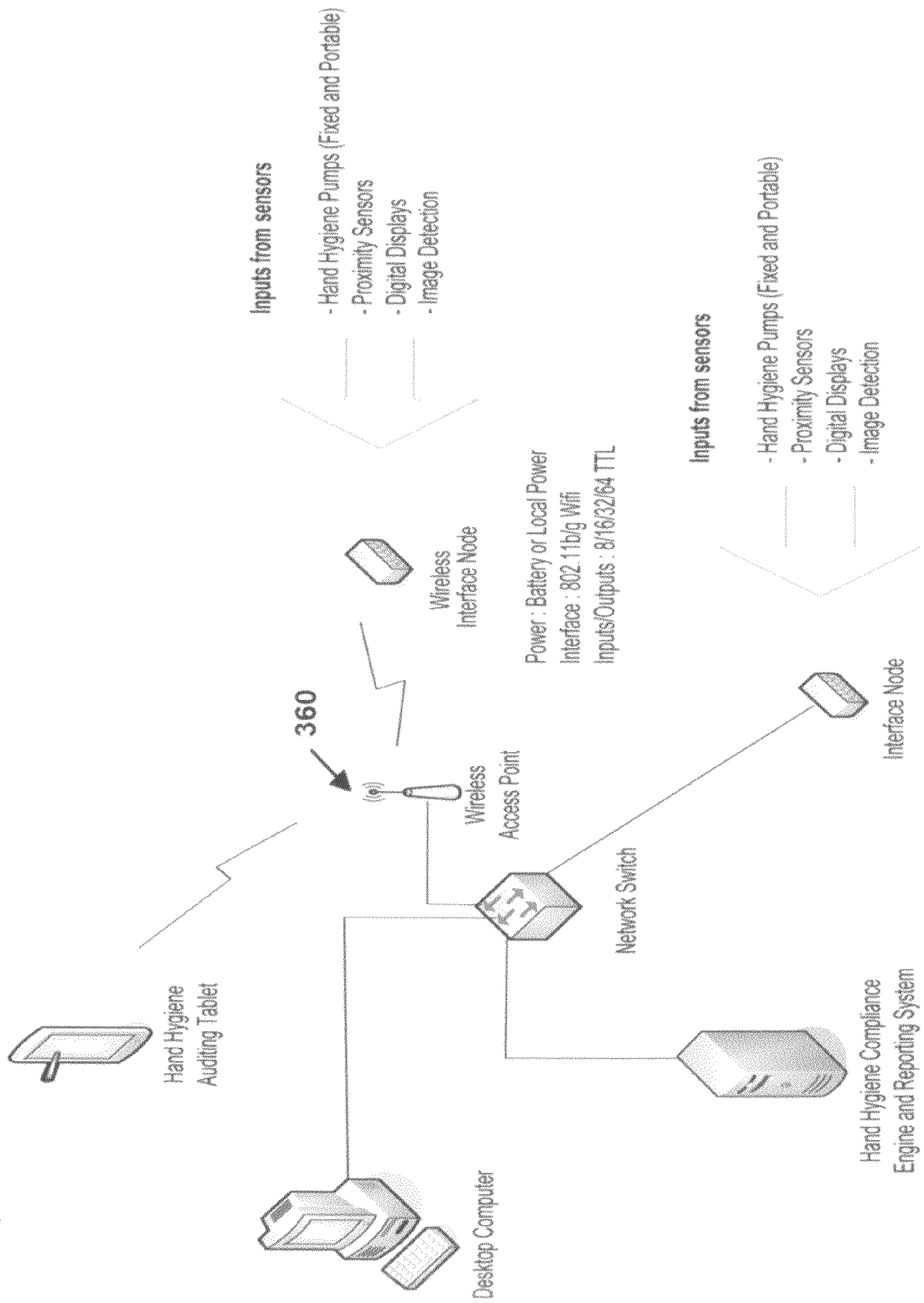
FIG. 16 is a flow chart of a communications network usable for compiling and maintaining a data base within a three dimensional protocol monitoring system 100.

FIG. 16 is a flow chart illustrating the operation of the three dimensional protocol monitoring system 100 data base as shown. The elements of the system are designed to compile information as to patient activity and safety and institutional hygiene protocol compliance by care-givers and visitors, and to cause selected signals to be generated and certain information recorded depending on whether a health care worker or other persons has been compliant with said protocol. The communications configuration is to be bi-directional in nature with the primary controller 360 so as to be capable of acquiring information from the systems associated sensors, compile and record such information and make such information available on associated fixed and portable information display and monitoring devices to include desktop computers, tablets, PDA's and cell phones.

EXAMPLE 1

In a first situation, a health care worker with a wearable monitor 220 enters a room and is detected by the three dimensional imaging assembly 400 associated with the primary controller 460. In this example, the system detection area 888 surrounding the patient's is considered contaminated. The worker will be considered "contaminated" when he enters (or leaves) the contaminated area and the cross contamination contact 460 accordingly generates a low power signal to the wearable monitor 220 and/or portable monitor/sanitizer 250 if a portable sanitizer/monitor is used instead of a monitor. This signal causes the monitor to set to Logic #0. (It will be appreciated that the monitor will be already have been set to Logic #0 by station ID clearing signal 777 if the worker has previously been detected entering the patients room from any contaminated area without washing his hands or if too much time has elapsed since the previous hand washing.) The worker may proceed to perform duties within the room that are not in close proximity to the patient without receiving a warning or causing a violation to be noted though he has not washed his hands. Even if detected by the three dimensional imaging assembly 400 within system detection area 888 the preferred system further requires detection of the worker in the patient care area 840 or alternately, patient control area 860 in order to cause the generation of warning signals and/or cause the recording of a violation. If, however, the health care worker has not so actuated the portable monitor/sanitizer 250 within the required distance from the patient, as noted by the absence of a generated signal 239 identifying the fixed patient associated sanitizer or the HCW associated portable sanitizer as belonging to the tracked HCW, the primary controller 460 will cause a record of a violation to be made and generate a warning signal upon receipt of signals from the three dimensional imaging assembly 400. It may also cause a warning signal to be generated or displayed on the portable monitor/sanitizer 250. While the preferred system require hand sanitation within a predetermined time as well as within a predetermined area, it can be configured to operate without a time requirement so long as the portable monitor/sanitizer 250 is actuated within the patient control area 860 and before the health care worker comes into close proximity or contact with the patient. Detection of the worker by the three dimensional protocol monitoring system 100 within system detection area 888 causes a hand washing reminder or other message to be displayed on or broadcast by the primary controller 460, but no warning signals are generated or violations recorded upon such detection.

EXAMPLE 2

In a second situation, a health care worker enters a patient's room and then uses the fixed base sanitizer 500 operatively associated with patient and preferably located within patient control area 860 in accordance with required hygienic protocol. The health care worker is detected by the patient care area three 840 by three dimensional imaging assembly 400 operatively associated with primary controller 460 in patient control area 860.

An augmented reality Avatar with an associated image value representing the HCW is generated. The sanitizer's activation causes the generation of a signal 266 that causes the worker's monitor to reset to Logic #1 from Logic #0 and the monitor and/or sanitizer display 218 and annunciator 418 associated with primary controller 460 to show a message indicating hand washing compliance while changing the logic level associated with the Avatar to logic #1. The annunciator 418 associated with the primary controller 460 is caused to generate a message such as "Sanitized. Such activation of the primary controller by detection of HCW entering system detection area 888 or patient control area 860 may also cause other information to be displayed by the primary controller annunciator such as the patient's name, drug allergies or special care requirements. Such information may be entered directly or independently by the querying of the patient's electronic records. This type of information may be displayed without such detection activation if desired, or through the use of other HCW or patient-operated controls (not shown).

EXAMPLE 3

In a third situation, a health care worker enters a system detection area 888 and a hand washing reminder message is displayed by the primary controller following detection in the patient care area by three dimensional protocol monitoring system 100. The worker, in this case, has washed his hands using the fixed base sanitizer 500 associated with the patient and/or room, but has allowed too much time to elapse since such washing. The annunciator 418 on the three dimensional imaging assembly 400 is accordingly caused to illuminate or flash to signify that excessive time has elapsed, and the monitor status changes from Logic #1 to Logic #0. The worker then proceeds to near proximity of the patient, i.e. within arm's length of the patient or their patient's support apparatus, and such proximity is detected by three dimension image processor 490. This causes the primary controller 460 to transmit a signal. Upon receipt of this signal a caution message is displayed on one or more of the annunciators associated with the primary controller. If the health care worker does not vacate the patient care area 840 within a certain period of time, an audible alarm will be generated by the speaker 249 associated with the primary controller. An appropriate message may also be displayed on the monitor 218. Violation of protocol will cause the recordation of the image of the violator including time, date and patient identification in the fixed or removable memory 466 of three dimensional imaging assembly 400.

EXAMPLE 4

A fourth possible situation involves a patient development that requires immediate attention. A health care worker enters the patient control area 860, is detected by the three dimensional imaging assembly 400 associated with the primary controller 460 and receives a cautionary or reminder message on the annunciator 418. The HCW has not washed his hands, and his portable monitor/sanitizer 250 is set to Logic #0 in the manner described above. He then comes in close proximity to or contact with the patient, as detected by three dimensional IR imaging device 440. The primary controller 460 receives a signal indicating the worker has not complied with hand washing rules. It then causes warnings to be displayed on annunciator 418 and/or the displays. In order to allow the worker to proceed without distraction, the three dimensional protocol monitoring system 100 may be placed in a standby mode by activating the pause switch 240 located on the portable sanitizer or the standby switch (not shown) on the three dimensional imaging assembly 400 This action causes a resetting of the three dimensional protocol monitoring system 100 to a non-monitoring standby status as well as causing the primary controller to replace the previous cautionary message displayed on the various operatively associated annunciators with a warning/alarm message declaring that an emergency is in progress. No further warnings, alarms, or other messages will be caused to be displayed on annunciators or other components of the system until it is reset to the normal operating mode. The actions in the patient care area contained within system detection area 888 subsequent to placing the system in a standby mode may be digitally recorded by the VGA color camera 430 and/or audio recording (not shown) and may be stored in fixed or removable memory 466 for future forensic examination.

EXAMPLE 5

In a sixth situation, a person who is not wearing an ID monitor enters the system detection area 888 where he is detected by the patient care three dimensional imaging assembly 400. The primary controller annunciator 418 is caused to generate a preselected message such as a hand washing reminder. The person proceeds to the patient care area 840 where his presence is determined by logic within three dimension image processor 490. Upon controller receiving no such signal indicating the person has used the fixed base sanitizer 500 or portable monitor/sanitizer 250 a warning signal is generated by one or more of the annunciators in the three dimensional protocol monitoring system 100. If HCW fails to respond at this point, a more compelling warning can be generated by the system and the nursing station can be alerted and a recording of the violation generated and compiled. If, as in this example, the absence of a monitor is considered a violation of protocol, the event and its time are recorded by the three dimensional imaging assembly 400. The person's exit from the patient care area monitored by the imaging assembly allows the three dimensional protocol monitoring system 100 to return to its normal operating mode, and video recording will discontinue a short time thereafter.

EXAMPLE 6

In a sixth situation, a visitor enters the patient control area 860 while wearing a wearable monitor 220. The visitor is detected by the three dimensional imaging assembly 400, causing the primary controller 460 to display a message on the associated annunciators reminding the visitor to wash his hands. The visitor then employs the fixed base sanitizer 500, causing the display 218 on the wearable monitor 220 to provide a compliance indication. The visitor, having complied with the required hand washing protocol, proceeds to within arm's length of the patient and is detected by three dimension image processor. The primary controller 360, having received input signals from both the imaging assembly 400 and an operatively associated sanitizer within a predetermined period of time, sends a signal to portable and fixed sanitizer indicating satisfactory hygiene protocol compliance by said visitor. Receipt of the signal 266 causes a message to be generated by any and all associated annunciators. The message can thank the visitor for washing his hands, remind the visitor to keep the visit short, and/or provide other information such as patient visiting hours. Subsequent activities, such as leaving the patient' bedside as determined by the imaging assembly may cause the generation of further messages on the annunciators such as a reminder to wash his hands again upon departure.

The primary controller can be linked thereto by wired or wireless connection. It can be combined with the fixed base sanitizer 500. In order to avoid disturbing a sleeping patient, the primary and proximity controllers can be programmed so that they do not cause the patient to be disturbed when a health care worker enters the patient care area. For example, the illumination of displays can be reduced during nighttime hours and audible signals eliminated during such time. The displays can be located in parts of a room where a resting patient will not be disturbed by them or where they are positioned or shielded from a patient's view.

Continuous monitoring of the patient is provided by the three dimensional protocol monitoring system 100 irrespective of whether the persons who may come into contact with the patient are wearing monitors or not. As discussed above, hand sanitizing is accomplished through the use of either stationary or portable sanitizers. The fixed base sanitizer 500 as described above transmits an encoded compliance signal 509 to the primary controller upon actuation of the sanitizing sensor 508, causing annunciators 418/518 as well as the display 218 on the portable sanitizer to indicate compliance with the institution's hand washing protocol. The fixed base sanitizer 500 is also capable of receiving a signal 266 from primary controller that is generated in response to the generation of an image value identification code 444. This identification signal includes processed information that allows the association of the person using the sanitizer to a particular Avatar to be recorded. Similarly, a sanitizer equipped with a three dimensional IR imaging device 440A may transmit the operation and image of the person actuating the sanitizer to the primary controller via encoded compliance signal 509. Since the primary controller 460 may receive the encoded compliance signal 509 directly from the fixed base sanitizer 500 in the preferred embodiment, the primary controller may integrate the information regarding the activity of each sanitizer and the hand washing activity of the health care worker. The monitoring of hand washing compliance may be accomplished through means other than the sanitizing devices as disclosed. For example, a sensor may be incorporated as part of a sink and faucet assembly 510 for determining whether a person has washed his hands as demonstrated in Deutsch U.S. Pat App. 61/459,427, which is incorporated by reference herein. A successful hand washing may occur when the person has stood before a sink for a selected period of time, dispensed soap, animated their hands in such a manner to reflect proper handwashing. Hand washing sensors and associated transmitters of compliance signals may also be included in devices such as automated alcohol or alcohol towelette dispensers, antiseptic dispensers, UV lights, glove dispensers or other monitored devices that may be used to sanitize hands.

In the preferred embodiment, the portable sanitizer is associated with a particular worker and the fixed base sanitizer 500 is associated with a particular patient, room or patient care area. When the worker approaches a patient, he first enters the system detection area 888 thereby triggering detection by the three dimensional imaging assembly 400. The health care worker's monitor, if not in Logic #0, is set to Logic #0 by the station ID clearing signal 777 associated with the primary controller upon detection of the worker by the three dimensional IR imaging device 440. Upon receipt of the sanitizer encoded compliance signal 509, the primary controller will compare the sanitizer identity code with pre-programmed acceptable codes associated with the patient or patient's location. If the code is acceptable, the annunciator 418 on the imaging assembly can signify compliance with the institution's hand washing protocol. As discussed above, the system may be configured such that the fixed base sanitizer 500 communicates directly with the primary controller 460, providing sanitizer identification information thereto as well as the identification, via image value, of the user of the sanitizer. Detection of HCW that has not sanitized but is detected in patient care area 840 will cause a response indicating non-compliance (Logic #0), such action will cause the generation of contamination warnings and record the time of the violation, the identity of the violator if known by imaging or other means e.g. RFID identity badge and the identification of the patient. It may also cause the actuation of the VGA color camera 430, thereby identifying any violator who may or may not be wearing a monitor.

In lieu of using a wearable monitor 220 or similar device to transmit worker identification information to the three dimensional protocol monitoring system 100, the identity of the health care worker may instead be provided to the fixed base sanitizer 500 biometric means (not shown) such as fingerprint recognition, an identity card with a magnetic strip or bar coding, or keypad input. The health care, worker's identity and the specifics of the hand washing event are then recorded by the sanitizer and transmitted to the primary controller 460 for subsequent comparison to an identity input of the worker obtained prior to the HCW reaching the system detection area 888 or entering the patient care area 840. This action can be accomplished following prompting from the annunciator 418 of the primary controller 460. Activation of the sanitizer and the matching of the worker identifying composite image value and the worker identifying image value identity associated with the sanitizer by the primary controller 460 will confirm compliance with the required hand washing protocol.

The patient area three dimensional IR imaging device 440 may be employed for causing the primary controller 460 to generate different messages as described above. Sequential detection of the HCW in patient control area 860 and then in patient care area 840 will cause the primary controller 460 to determine that a person is approaching a patient and attempt to determine whether that person has complied with required hand washing procedures. Alternately, detection of the HCW in patient care area 840 and then in patient control area 860 will cause the primary controller 460 to determine that a person is leaving the patient, attempt to determine whether that person has complied with required hand washing procedures by activating a sanitizer and if not, causes the primary controller 460 to generate a message advising the worker hygiene protocol has been violated. Detection within the system detection area 888 causes the primary controller 460 to generate a message advising the worker that the area is monitored and/or reminding the worker to wash his hands if he intends to contact the patient. If contact with a known contaminated surface e.g. wall is indicated by positional deterministic algorithms of the image processing system, while the HCW or visitor is in the system detection area 888 subsequent to sanitizing, they will be instructed to re-sanitize prior to patient contact. Failure to comply will be considered a violation of hygiene protocol. The field of view of the three dimensional IR imaging device 440 is configured so as to be able to detect any persons close enough to the patient so as to present an immediate threat of contamination. The primary controller 460 in the preferred system communicates directly with displays capable of providing advisory or warning messages to a person in the patient's room is preferred for successful operation as only a health care worker or visitor will be likely to view such warnings. Moreover, such an arrangement helps ensure that warnings will not be generated or violations recorded by anything other than a person who comes in the room to actually treat or contact the patient.

The three dimensional imaging assembly 400 is operatively associated with the patient, and will accordingly view the patient whether he is in bed or elsewhere. It is intended to sense when a person is in near contact with (within arm's length or less) or touching a patient or an article worn by or covering the patient. When a person either touches or comes very close to the patient, near contact is then determined by system's firmware's 492's ability to recognize the positional and kinematic relationship between the patient and the HCW.

In addition to promoting hygienic compliance, the monitoring system 100 may alternately be employed for restricting access to a monitored area to a selected group of personnel. The system provides the means for detection of all persons entering such an area irrespective of whether they are wearing monitoring devices or not. A system detection area 888 may be designated as a restricted access area 888, in which a highly contagious patient is located or a neonate ward. The restricted area may be rectangular, but does not necessarily have to be in any particular geometric form. A three dimensional imaging assembly 400 is preferably employed to provide additional logic, as described above. A digital recording system incorporating a VGA color camera 430 and fixed or removable memory 466 records protocol violations as determined by the primary controller 460. The three dimensional imaging assembly 400 will initially recognize the presence of a health care worker or any other person within a general predefined area. This may cause the primary controller 460 to display a message conveying the fact that the area is monitored. Once a three dimensional IR imaging device 440 detects the presence of a person by a disturbance within its field of optical sensitivity, the primary controller 460 will transmit a signal 266 and subsequently search for a responding signal 239 from wearable monitor 220. Upon receiving a signal 239 from a wearable monitor 220 that has been pre-encoded with the image value of a person with permitted access per institutional protocol to the restricted area, a message indicating access compliance will be displayed by the annunciator operatively associated with the primary controller. If a properly encoded signal 239 which includes an image value associated with the HCW/visitor bearing said monitor does not match the image value derived from the HCW/visitor detected within the scene being viewed by the three dimensional imaging assembly 400, or if no responsive signal 239 is received, a warning can be displayed indicating that an unauthorized entrance has been made violating institutional protocol. The VGA color camera 430 within three dimensional imaging assembly 400 can be actuated to record the activity of the violator on the fixed or removable memory 466 of the primary controller 460 or alternately, elsewhere via Wi-Fi Bluetooth or other wireless means. Additional contact sensors e.g. charge transfer devices may be employed as illustrated by Deutsch U.S. Pat. No. 7,893,842 which is incorporated by reference herein to further define the restricted area and to possibly cause the generation of additional warnings or alarms. All monitors, sensors, sanitizers and other elements of the system 100 are preferably designed for easy cleaning or disinfecting. Bactericidal materials may be incorporated into the monitors or portions thereof to help ensure patient and worker safety.

EXAMPLE 7

In a seventh situation, a patient located within the patient care area scene as viewed by the three dimensional IR imaging device 440 has left or has attempted to leave their bed. The action and location deterministic algorithms of the image processing system within the three dimension image processor 490 and system's firmware 492 provide the three dimensional imaging assembly 400 with the capabilities of the monitoring the position and actions of the patient and determining by referencing a known set of possible positions and movements, whether such patient movements, locations or positions are within acceptable parameters so as to comply with institutional protocol. As an example, the placement of an unattended patient supine in the middle of a bed may be considered typical in a hospital room. Any deviation of this image, as seen by the three dimensional IR imaging device 440, may be cause to for the imaging assembly to focus either its cameras and/or its computational capabilities on said patient and initiate tracking of the patient's location and movements. Per requisite protocol the patient may be allowed to leave their bed. Thereby detection of such actions by three dimensional IR imaging device 440 and interpretation of acquired images by deterministic algorithms in three dimension image processor 490 would cause no alarm to be generated. Alternately, the patient may be restricted to their bed. Any attempt by the patient to leave their bed as determined by specific movements of their body e.g. their legs are over the side of the bed as referenced against a set of known deterministic actions captured by three dimension image processor 490 may be recognized as an attempt to leave their bed an cause the generation of a message indicating same on any one of the operatively associated annunciators. Additionally, against hospital protocol, a patient may have unsuccessfully attempted to leave their bed as indicated in FIG. 4 and placed themselves in harm's way. e.g. determining the patient's body partially out of bed or on the floor within the patients room. Images of the patient, as acquired from three dimensional IR imaging device 440, processed by deterministic algorithms associated with three dimension image processor 490 may recognize this situation a being an medical priority requiring immediate assistance and may cause three dimensional imaging assembly 400 to generate an associated message thereby indicating that a medical priority situation exits and immediate assistance is required. An additional application of monitoring patient movements and locations may be the monitoring of the patients movements while confined to bed. Certain patient movements, while confined to bed, as detected by the three dimensional IR imaging device 440 and interpreted by the deterministic logic of the three dimension image processor 490 may be indicative of a medical emergency requiring immediate medical attention. Examples include rapid uncontrolled movements of the extremities with limited travel may be indicative of a seizure. Less dramatic movements including movements of the torso may be indicative of a restless patient. Detection of these actions may cause the generation of different messages from the preceding situation message e.g. "This is a medical emergency". Various messages to be displayed on the associated annunciators may be associated with specific actions by the patient or transmitted wirelessly to remote locations. Additionally, the system 100 provides a means via the included VGA color camera 430 and associated fixed or removable memory 466 for recording these actions for forensic analysis. The determinations of patient actions and locations presented here are not to be considered the only actions that may monitored and should be considered as reference examples only.

What is claimed is:
1. A method for monitoring protocol compliance comprising:
    capturing a three dimensional image of one or more select persons within a monitored area via that imaging system;

generating feature vectors uniquely associated with the physical features within those images of the one or more select persons;

creating an avatar from the one or more select person's feature vectors of the one or more selected persons as representative;

creating an identify image value representing that avatar;

associating and encoding those image values to an identification monitor associated with that one or more persons; and comparing the image value of that person with that image value of the identification monitor thereby determining if that person enters a monitored area or contacts a specified imaged object thereby changing the status of the person.

2. A method as described in claim 1, further comprising the steps of:

determining whether the person possesses a required identification monitor by detection of all or part of the associated encoded image value based identification code available from that identification monitor representing that person;

generating a control signal indicating that person is not wearing an encoded identification monitor if the image based identification code is absent;

tracking the location of the person's avatar determining when the person enters and leaves a monitored area; and thereby changing the status of the person.

3. A method as described in claim 1, further comprising the step of:

determining whether the avatar has come within a first distance of a predetermined location within a monitored area;

determining whether the avatar has come within a second distance closer than the first to the predetermined location; and generating a control signal following detection of the avatar sequentially coming within the first and second distances of the specific location and thereby changing the status of the avatar.

4. A method as described in claim 1, further comprising the steps of;

determining whether that person's identification monitor has generated an identifiable image value associated control signal thereby evidencing use of an operatively associated device by that person; and altering that person's avatar's indicated status based on use of that device by that persons.

5. A method as described in claim 1, further comprising the step of;

generating a caution or warning control signal upon determining the avatar's near proximity to a specific surface or object within the monitored area: and altering that persons avatar's indicated status based on a control signal reflecting that persons location and a control signal evidencing concurrent use of an associated monitored device.

6. A method as described in claim 1, further comprising the step of:

a visible or infra-red imaging system including the capacity for three dimensional imaging through the use of one or more cameras.

7. A system for monitoring protocol compliance comprising:

A visible or infra-red electro-optical imaging system and cooperating processor capable of capturing a three dimensional image of one or more select persons within a monitored area via that imaging system;

a processing assembly for determining whether the one or more persons moves or contacts an object, location or position by extracting and analyzing motion and position from the three dimensional image;

a processing assembly for generating a set of feature vectors uniquely associated with the physical features within that images of the one or more select persons;

a processing assembly for creating an avatar from the one or more select persons feature vectors of the one or more selected persons as representative;

processing assembly for generating a unique communicable identifying image value representing that avatar;

a processing assembly for wirelessly encoding those image values into a portable identification monitor representing that one or more persons; and a processing assembly for tracking and identifying that avatar via that identifying image value.

8. A system as described in claim 7, further comprising the step of;

a processing assembly capable of determining the image values of that identification monitor in possession of that persons;

a processing assembly capable of determining the image values of that avatar representing that person; and a processing assembly operatively associated with an annunciator for indicating the association.

9. A system as described in claim 8, further comprising the step of;

a processing assembly for determining an avatars access to a privileged area via correlating image value of the portable monitor in their possession to an external data base of acceptable image values for that monitored area.

10. A system as described in claim 9, further comprising;

a processing assembly for determining a correlation of that persons identification monitor's image value with a data base of known person's avatar image values; and an operatively associated annunciator for displaying a first message indicating same.

11. A system as described in claim 9, further comprising;

a processing assembly for determining a lack of correlation of that avatars identification image value with a data base of known person's avatar image values; and an operatively associated annunciator for displaying a second message indicating same.

12. A system as described in claim 7, further comprising;

a processing assembly for determining a positive correlation of that persons identification monitor's image value with a data base of known person's avatar image values allowable in a specific monitored area; and an operatively associated annunciator for indicating same on that persons monitor.

13. A system as described in claim 7, further comprising;

a processing assembly for determining a negative correlation of that persons avatar's image value with a data base of known person's avatar image values; and an operatively associated annunciator for displaying a third message indicating same.

14. A system as described in claim 7, further comprising the steps of:

a processing assembly for determining whether the person possesses the required identification monitor and identification code when in a predetermined area including;

a processing assembly for communicating with the processing assembly of that identification monitor representing that person;

a processing assembly for generating a control signal indicating that person is not wearing an identification monitor if the monitors image based identification code is absent or an incorrect image value identification code is present when viewing a select persons; and a processing assembly for tracking the location of that person's avatar via their image value and determining when that person enters and leaves a specific location within a monitored area thereby changing the status of that avatar.

15. A method for monitoring hygiene compliance comprising:

capturing a three dimensional image of one or more select persons within a room via that imaging system;

determining whether the one or more persons moves or contacts an object, location or position by extracting and analyzing motion and position from the three dimensional image;

generating feature vectors uniquely associated with the physical features of the one or more select persons image;

creating an avatar from the one or more select person's feature vectors of the one or more selected persons as representative;

creating an identify image value representing the avatar;

associating and conveying those image values with an that one or more persons identification monitor;

generating a message reactive to the correlating of an image value associated signal from the identification monitor evidencing use of a specific sanitizer and the image value of that person's avatar within a monitored area.

16. The method of claim 15, further comprising the step of:

determining whether the avatar has come within a first distance of a patient's location;

determining whether the avatar has come within a second distance closer than the first to the patient's location;

determining via the detection of a unique signal associated with that image value identifying that person's monitor thereby evidencing use of their sanitizer; and generating a control signal following detection of the person sequentially coming within the first and second distances of the patient without having caused the actuation of the sanitizing device; and the step of generating a message and indicating via an annunciator proper compliance with sanitizing protocol evidenced by compliant activation of the sanitizing device.

17. A system for monitoring hygiene compliance comprising:

a processing assembly for capturing a three dimensional image of one or more select persons within an area via that imaging system;

a processing assembly for determining whether the one or more persons moves or contacts an object, location or position by extracting and analyzing motion and position from the three dimensional image;

a processing assembly for generating an avatar of that persons from feature vectors of that persons image;

a processing assembly for generating and image value from the avatar of the one or more select persons;

a processing assembly for tracking the avatar's location via the identifying image value;

a processing assembly for conveying that identifying image value to and from that person's portable monitor:

a sanitizing device operatively associated with the monitor; and an indicator device operatively associated with a processing assembly for detecting a monitor's image value based control signal evidencing use of a specific sanitizer.

18. The system as described in claim 17, further comprising;

a processing assembly operable for determining whether that sanitizer was actuated in a specified location by the avatar within a monitored area; and a processing assembly for generating a control signal operatively associated with an annunciator thereby indicating the avatars hygienic status based on an association between the received encoded image value of the monitor evidencing activation of that sanitizer and the determined location of that persons avatar's image value within that monitored area.

19. The system as described in claim 17, further comprising;

a processing assembly operable for determining, compiling and recording a HIPAA patient privacy rule compliant data table reflecting individual and collective compliance and non-compliance of that persons avatar with required hygienic protocol; and a processing assembly operatively associated with an annunciator for graphically displaying that information of that data table.

20. The system as described in claim 17, further comprising;

an annunciator operatively associated with a processing assembly for displaying a first message indicating protocol compliant use of that specific sanitizer as evidenced by activation of the sanitizer in a predetermined area during a pre-determined time interval per hygiene protocol requirements by that avatar.

21. The system of claim 17, further comprising;

an annunciator operatively associated with a processing assembly for displaying a second message indicating non-compliant hygiene protocol use of that specific sanitizer as evidenced by the lack of a activation of the sanitizer within a specified time interval within a predetermined area when responding to a control signal indicating activation of the sanitizer outside the required protocol area by the avatar.

22. The system as described in claim 17, further comprising;

a processing assembly operable for determining and generating a control signal associated with an annunciator upon determining that contact or near contact by the avatar with a specific pre-determined surface or object within the monitored area has occurred prior to or subsequent to detection of a signal evidencing activation of the sanitizing device.

23. A system as described in claim 17, further comprising;

a processing assembly operable for determining the identity of a person within a monitored area via the determination of the image value of that person's avatar within a monitored area;

a processing assembly operable for associating that image value with a data base of known person's avatar's image values; and a processing assembly operatively associated with an annunciator for indicating a positive association with a data base of known avatar's image values thereby identifying the person or indicating a lack of identification thereof.

24. A system as described in claim 17, further comprising;
a processing assembly operable for determining the identity of a person within a monitored area via determination of the image value of that person's monitor within a monitored area;
a processing assembly operable for associating that image value with a data base of known avatar's image values; and
a processing assembly operatively associated with an annunciator for indicating a positive association with a data base of known avatar's image values thereby identifying the person or indicating a lack of identification thereof.

25. A system as described in claim 17 wherein the electro-optical imaging system includes the capacity for generating a three dimensional image via one or more cameras.

26. A system for monitoring caregiver and patient protocol compliance comprising:
a sanitizing device;
a processing assembly operable for capturing a three dimensional image of one or more select persons within a room via that imaging system of one or more cameras;
a processing assembly for generating feature vectors uniquely associated with the visible physical features and characteristics of that one or more select persons;
a processing assembly operable for creating an avatar from the one or more select person's feature vectors of the one or more selected persons as representative;
a processing assembly for assigning an identifying image value to that person via from the feature vectors of that avatar;
a processing assembly operable for tracking and identifying that avatar via the identifying image value;
a processing assembly functionally responsive to specific images of kinematic hand motions of the avatar at the sanitizing device; and
a processing assembly operatively associated with an annunciator reactive to a control signal from the image processing assembly detecting and determining specific kinematic hand motions by the monitored avatar at the sanitizing device evidencing that persons hands being sanitized.

27. A system as described in claim 26, further comprising;
a processing assembly for determining the identity of a person within a monitored area via determination of the image value of that person's avatar within a monitored area;
a processing assembly for associating that image value with a data base of known avatar's image values; and
a processing assembly capable of generating a control signal operatively associated with an annunciator for indicating that avatars association with a data base of known avatar's image values thereby identifying that person or indicating a lack of identification of that person thereof; and
a processing assembly for associating that person's avatar with the determination of proper hand sanitizing per hygiene protocol by that avatar.

* * * * *